United States Patent
DeRosa et al.

(10) Patent No.: US 12,201,677 B2
(45) Date of Patent: Jan. 21, 2025

(54) MESSENGER RNA THERAPY FOR THE TREATMENT OF ORNITHINE TRANSCARBAMYLASE DEFICIENCY

(71) Applicant: Translate Bio, Inc., Lexington, MA (US)

(72) Inventors: Frank DeRosa, Lexington, MA (US); Michael Heartlein, Lexington, MA (US); Lianne Smith, Lexington, MA (US); Shrirang Karve, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 972 days.

(21) Appl. No.: 17/094,327

(22) Filed: Nov. 10, 2020

(65) Prior Publication Data

US 2021/0205421 A1    Jul. 8, 2021

Related U.S. Application Data

(62) Division of application No. 15/621,616, filed on Jun. 13, 2017, now Pat. No. 10,835,583.

(60) Provisional application No. 62/509,568, filed on May 22, 2017, provisional application No. 62/349,331, filed on Jun. 13, 2016.

(51) Int. Cl.
    *A61K 38/45*     (2006.01)
    *A61K 9/00*      (2006.01)
    *A61K 9/127*     (2006.01)
    *A61K 48/00*     (2006.01)
    *C12N 9/10*      (2006.01)

(52) U.S. Cl.
    CPC ............ *A61K 38/45* (2013.01); *A61K 9/0019* (2013.01); *A61K 9/1272* (2013.01); *A61K 48/0058* (2013.01); *C12N 9/1018* (2013.01); *C12Y 201/03003* (2013.01); *A61K 48/00* (2013.01)

(58) Field of Classification Search
    CPC .... A61K 38/45; A61K 9/0019; A61K 9/1272; A61K 48/0058; A61K 48/00; C12N 9/1018; C12Y 201/03003; A61P 3/00; A61P 43/00
    See application file for complete search history.

(56) References Cited

U.S. PATENT DOCUMENTS

| | | |
|---|---|---|
| 5,705,385 A | 1/1998 | Bally et al. |
| 5,976,567 A | 11/1999 | Wheeler |
| 5,981,501 A | 11/1999 | Wheeler et al. |
| 6,534,484 B1 | 3/2003 | Wheeler et al. |
| 6,815,432 B2 | 11/2004 | Wheeler et al. |
| 7,422,902 B1 | 9/2008 | Wheeler et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 8,101,741 B2 | 1/2012 | MacLachlan et al. |
| 8,188,263 B2 | 5/2012 | MacLachlan et al. |
| 8,236,943 B2 | 8/2012 | Lee et al. |
| 8,329,070 B2 | 12/2012 | MacLachlan et al. |
| 8,513,403 B2 | 8/2013 | MacLachlan et al. |
| 8,569,256 B2 | 10/2013 | Heyes et al. |
| 8,710,200 B2 | 4/2014 | Schrum et al. |
| 8,822,663 B2 | 9/2014 | Schrum et al. |
| 8,883,202 B2 | 11/2014 | Manoharan et al. |
| 8,980,864 B2 | 3/2015 | Hoge et al. |
| 9,051,567 B2 | 6/2015 | Fitzgerald et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |

(Continued)

FOREIGN PATENT DOCUMENTS

| | | |
|---|---|---|
| CA | 2807552 | 9/2012 |
| CN | 105658242 A | 6/2016 |

(Continued)

OTHER PUBLICATIONS

Cheng et al. "Codon Optimization of Gene Editing CRISPR-SaCas9 Augments Protein Expression in Human Liver Cells to Boost in vivo Therapeutic Application." The FASEB Journal 33.S1 (2019): 495-3. (Year: 2019).*

(Continued)

*Primary Examiner* — Titilayo Moloye
(74) *Attorney, Agent, or Firm* — LATHROP GPM LLP; James H. Velema, Esq.

(57) ABSTRACT

The present invention provides, among other things, methods of treating ornithine transcarbamylase (OTC) deficiency, including administering to a subject in need of treatment a composition comprising an mRNA encoding an ornithine transcarbamylase (OTC) protein at an effective dose and an administration interval such that at least one symptom or feature of the OTC deficiency is reduced in intensity, severity, or frequency or has delayed onset. In some embodiments, the mRNA is encapsulated in a liposome comprising one or more cationic lipids, one or more non-cationic lipids, one or more cholesterol-based lipids and one or more PEG-modified lipids.

24 Claims, 12 Drawing Sheets
Specification includes a Sequence Listing.

(56) References Cited

U.S. PATENT DOCUMENTS

| | | |
|---|---|---|
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,535 B2 | 8/2016 | de Fougerolles et al. |
| 9,428,751 B2 | 8/2016 | MacDonald et al. |
| 9,447,164 B2 | 9/2016 | Schrum et al. |
| 9,464,124 B2 | 10/2016 | Bancel et al. |
| 9,492,386 B2 | 11/2016 | MacLachlan et al. |
| 9,504,651 B2 | 11/2016 | MacLachlan et al. |
| 9,504,734 B2 | 11/2016 | Bancel et al. |
| 9,518,272 B2 | 12/2016 | Yaworksi et al. |
| 9,572,874 B2 | 2/2017 | Fotin-Mleczek et al. |
| 9,572,896 B2 | 2/2017 | Bancel et al. |
| 9,572,897 B2 | 2/2017 | Bancel et al. |
| 9,587,003 B2 | 3/2017 | Bancel et al. |
| 9,616,084 B2 | 4/2017 | Mutzke |
| 9,623,095 B2 | 4/2017 | Kallen et al. |
| D787,703 S | 5/2017 | Mayer |
| 9,636,301 B2 | 5/2017 | Weber |
| 9,655,955 B2 | 5/2017 | Hoerr et al. |
| 9,657,295 B2 | 5/2017 | Schrum et al. |
| 9,669,089 B2 | 6/2017 | Thess et al. |
| 9,670,152 B2 | 6/2017 | Payne et al. |
| 9,675,668 B2 | 6/2017 | Bancel et al. |
| 9,682,139 B2 | 6/2017 | Monoharan et al. |
| 9,683,233 B2 | 6/2017 | Thess |
| 9,687,550 B2 | 6/2017 | Manoharan et al. |
| 9,688,729 B2 | 6/2017 | Kramps et al. |
| 2002/0192651 A1 | 12/2002 | Wheeler et al. |
| 2003/0181410 A1 | 9/2003 | Wheeler et al. |
| 2004/0142025 A1 | 7/2004 | MacLachlan et al. |
| 2006/0008910 A1 | 1/2006 | MacLachlan et al. |
| 2006/0083780 A1 | 4/2006 | Heyes et al. |
| 2007/0135372 A1 | 6/2007 | MacLachlan et al. |
| 2009/0270481 A1 | 10/2009 | MacLachlan et al. |
| 2010/0041152 A1 | 2/2010 | Wheeler et al. |
| 2011/0244026 A1 | 10/2011 | Guild et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0082092 A1 | 3/2016 | Hoerr et al. |
| 2016/0089424 A1 | 3/2016 | Hoerr et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2016/0375137 A9 | 12/2016 | Manoharan et al. |
| 2017/0000858 A1 | 1/2017 | Fotin-Mleczek et al. |
| 2017/0000870 A1 | 1/2017 | Hoerr et al. |
| 2017/0000871 A1 | 1/2017 | Probst et al. |

(56) References Cited

U.S. PATENT DOCUMENTS

| | | |
|---|---|---|
| 2017/0002060 A1 | 1/2017 | Bolen et al. |
| 2017/0007702 A1 | 1/2017 | Heyes et al. |
| 2017/0014496 A1 | 1/2017 | Fotin-Mleczek et al. |
| 2017/0028059 A1 | 2/2017 | Baumhof et al. |
| 2017/0029847 A1 | 2/2017 | Thess |
| 2017/0042814 A1 | 2/2017 | Yaworski et al. |
| 2017/0056528 A1 | 3/2017 | De Fougerolles et al. |
| 2017/0056529 A1 | 3/2017 | Thess et al. |
| 2017/0065675 A1 | 3/2017 | Bancel et al. |
| 2017/0065727 A1 | 3/2017 | Fotin-Mleczek et al. |
| 2017/0114378 A1 | 4/2017 | Wochner et al. |
| 2017/0128549 A1 | 5/2017 | Fotin-Mleczek et al. |
| 2017/0136131 A1 | 5/2017 | Roy et al. |
| 2017/0136132 A1 | 5/2017 | Roy et al. |
| 2017/0143631 A1 | 5/2017 | Chen et al. |
| 2017/0143796 A1 | 5/2017 | Schrum et al. |
| 2017/0151333 A1 | 6/2017 | Heyes et al. |
| 2017/0157268 A1 | 6/2017 | Ansell et al. |
| 2017/0166905 A1 | 6/2017 | Eberle et al. |
| 2017/0173128 A1 | 6/2017 | Hoge et al. |
| 2017/0175129 A1 | 6/2017 | Roy et al. |
| 2017/0182081 A1 | 6/2017 | Mutzke |
| 2017/0182150 A1 | 6/2017 | Kallen et al. |

FOREIGN PATENT DOCUMENTS

| | | |
|---|---|---|
| CN | 106164248 A | 11/2016 |
| EP | 1519714 | 10/2010 |
| EP | 2449106 | 5/2012 |
| EP | 2338478 | 6/2013 |
| EP | 2823809 | 1/2015 |
| WO | WO2005/026372 | 3/2005 |
| WO | WO2005/121348 A1 | 12/2005 |
| WO | WO2009/127060 | 10/2009 |
| WO | WO2010042877 A1 | 4/2010 |
| WO | WO2011/068810 A1 | 6/2011 |
| WO | WO2011/141705 | 11/2011 |
| WO | WO2012/019168 | 2/2012 |
| WO | WO2012/135805 | 10/2012 |
| WO | WO2013/039857 | 3/2013 |
| WO | WO2013/039861 | 3/2013 |
| WO | WO2013/090186 A1 | 6/2013 |
| WO | WO2013/101690 | 7/2013 |
| WO | WO2013/126803 | 8/2013 |
| WO | WO2013/130161 | 9/2013 |
| WO | WO2013/151663 | 10/2013 |
| WO | WO2013/151664 | 10/2013 |
| WO | WO2013/151666 | 10/2013 |
| WO | WO2013/151667 | 10/2013 |
| WO | WO2013/151668 | 10/2013 |
| WO | WO2013/151670 | 10/2013 |
| WO | WO2013/151671 | 10/2013 |
| WO | WO2013/151672 | 10/2013 |
| WO | WO2013/151736 | 10/2013 |
| WO | WO2013/185069 | 12/2013 |
| WO | WO2014/113089 | 7/2014 |
| WO | WO2014/144039 | 9/2014 |
| WO | WO2014/144711 | 9/2014 |
| WO | WO2014/144767 | 9/2014 |
| WO | WO2014/152027 | 9/2014 |
| WO | WO2014/152030 | 9/2014 |
| WO | WO2014/152031 | 9/2014 |
| WO | WO2014/152211 | 9/2014 |
| WO | WO2014/152540 | 9/2014 |
| WO | WO2014/158795 | 10/2014 |
| WO | WO2014/159813 | 10/2014 |
| WO | WO2015/006747 A2 | 1/2015 |
| WO | WO2015/051169 | 1/2015 |
| WO | WO2015/051173 | 1/2015 |
| WO | WO2015/058069 | 1/2015 |
| WO | WO2015/048744 | 4/2015 |
| WO | WO2015/085318 | 6/2015 |
| WO | WO2015/089511 | 6/2015 |
| WO | WO 2015/164773 A1 | 10/2015 |
| WO | WO2015/011633 | 1/2016 |
| WO | WO2016/054421 | 4/2016 |
| WO | WO2016/070166 A2 | 5/2016 |
| WO | WO2016/071857 | 5/2016 |
| WO | WO2016/077123 | 5/2016 |
| WO | WO2016/077125 | 5/2016 |
| WO | WO2016/0706166 A2 | 5/2016 |
| WO | WO2016/118724 | 7/2016 |
| WO | WO2016/118725 | 7/2016 |
| WO | WO2016/154127 | 9/2016 |
| WO | WO2016/164762 | 10/2016 |
| WO | WO2016/183366 A2 | 11/2016 |
| WO | WO2016/197132 A1 | 12/2016 |
| WO | WO2016/197133 A1 | 12/2016 |
| WO | WO2016/201377 A1 | 12/2016 |
| WO | WO2017/019891 A2 | 2/2017 |
| WO | WO2017/049074 A1 | 3/2017 |
| WO | WO2017/049275 A2 | 3/2017 |
| WO | WO2017/049286 A1 | 3/2017 |
| WO | WO2017/102010 A1 | 6/2017 |
| WO | WO2017/103088 A1 | 6/2017 |
| WO | WO2017/108087 A1 | 6/2017 |
| WO | WO2017/109134 A1 | 6/2017 |
| WO | WO2017/109161 A1 | 6/2017 |
| WO | WO2019/207060 A1 | 10/2019 |

OTHER PUBLICATIONS

Wang et al. "Preclinical evaluation of a clinical candidate AAV8 vector for ornithine transcarbamylase (OTC) deficiency reveals functional enzyme from each persisting vector genome." Mol Genet Metab. Feb. 2012;105(2):203-11. (Year: 2012).*

Mauro et al. "A critical analysis of codon optimization in human therapeutics." Trends Mol Med. Nov. 2014;20(11):604-13. (Year: 2014).*

Ward et al. "Codon optimization of human factor VIII cDNAs leads to high-level expression." Blood . Jan. 20, 2011;117(3):798-807. (Year: 2011).*

Krauss et al. "A cDNA clone for the precursor of rat mitochondrial ornithine transcarbamylase: comparison of rat and human leader sequences and conservation of catalytic sites." Nucleic Acids Res Feb. 11, 1985;13(3):943-52. (Year: 1985).*

Ye et al. "Differences in the human and mouse amino-terminal leader peptides of ornithine transcarbamylase affect mitochondrial import and efficacy of adenoviral vectors." Hum Gene Ther . Jun. 10, 2001; 12(9):1035-46. (Year: 2001).*

U.S. Appl. No. 15/621,616 2018/0008680 U.S. Pat. No. 10,835,583, filed Jun. 13, 2017 Jan. 11, 2018 Nov. 17, 2020, Frank DeRosa, Messenger RNA Therapy for the Treatment of Ornithine Transcarbamylase Deficiency.

U.S. Appl. No. 17/094,327 2021/0205421, filed Nov. 10, 2020 Jul. 8, 2021, Frank DeRosa, Messenger RNA Therapy for the Treatment of Ornithine Transcarbamylase Deficiency.

Schmitz et al., "Purification of nucleic acids by selective precipitation with polyethelyne glycol 6000", Analytical Biochemistry, 2006, 354(2): 311-313.

Alton et al., "A randomised, double-blind, placebo-controlled trial of repeated nebulisation of non-viral cystic fibrosis transmembrane conductance regulator (CFTR) gene therapy in patients with cystic fibrosis," Efficacy and Mechanism Evaluation, Jul. 2016, vol. 3, No. 5, ISSN 2050-4365.

Database EMBL, Database Accession No. BAW43135 (Dec. 5, 2013).

International Search Report and Written Opinion for PCT/US17/37237 mailed Aug. 21, 2017, 17 pages.

Kowalski et al. "Delivering the Messenger: Advances in Technologies for Therapeutic mRNA Delivery." Mol Ther. Apr. 10, 2019;27(4): 710-728. (Year: 2019).

Matsui et al. "Messenger RNA-based therapeutics for the treatment of apoptosis-associated diseases." Sci Rep. Oct. 28, 2015;5:15810. (Year: 2015).

Moscioni et al., "Long-term correction of ammonia metabolism and prolonged survival in ornithine transcarbamylase-deficient mice following liver-directed treatment with adeno-associated viral vectors", Mol Ther., Jul. 2006, vol. 14, No. 1, pp. 25-33.

(56) References Cited

OTHER PUBLICATIONS

Trepotec et al. "Delivery of MRNA Therapeutics for the Treatment of Hepatic Diseases." Mol Ther. Apr. 10, 2019;27(4): 794-802. (Year: 2019).

Wang et al., "Preclinical evaluation of a clinical candidate AAV8 vector for ornithine transcarbamylase (OTC) deficiency reveals functional enzyme from each persisting vector genome", Mol Genet Metab., Feb. 2012, vol. 105, No. 2, pp. 203-211.

Wang et al., "Sustained correction of OTC deficiency in spf( ash) mice using optimized self-complementary AAV2/8 vectors", Gene Ther., Apr. 2012, vol. 19, No. 4, pp. 404-410.

\* cited by examiner

SEQUENCE LISTING

<160> NUMBER OF SEQ ID NOS: 15

<210> SEQ ID NO 1
<211> LENGTH: 1065
<212> TYPE: RNA
<213> ORGANISM: Artificial Sequence
<220> FEATURE:
<223> OTHER INFORMATION: Chemically synthesized nucleotide

<400> SEQUENCE: 1
augcuguuua aucugaggau ccuguuaaac aaugcagcuu uuagaaaugg ucacaacuuc     60

| | |
|---|---|
| augguucgaa auuuucggug uggacaacca cuacaaaaua aagugcagcu gaagggccgu | 120 |
| gaccuucuca cucuaaaaaa cuuuaccgga aagaaauua aauauaugcu augscuauca | 180 |
| gcagaucuga aauuuaggau aaaacagaaa ggagaguauu ugccuuuauu gcaagggaag | 240 |
| uccuuaggca ugauuuuuga aaaagaagu acucgaacaa gauugucuac agaaacaggc | 300 |
| uuugcacuuc ugggaggaca uccuuguuuu cuuaccacac aagauauuca uuugggugug | 360 |
| aaugaaaguc ucacggacac ggcccgugua uugucuagca uggcagaugc aguauuggcu | 420 |
| cgaguguaua aacaaucaga uuuggacacc cuggcuaaag aagcauccau cccaauuauc | 480 |
| aaugggcugu cagauuugua ccauccuauc cagauccugg cugauuaccu cacgcuccag | 540 |
| gaacacuaua gcucucugaa aggucuuacc cucagcugga ucggggaugg gaacaauauc | 600 |
| cugcacucca ucaugaugag cgcagcgaaa uucggaaugc accuucaggc agcuacucca | 660 |
| aagguuaug agccggaugc uaguguaacc aaguuggcag agcaguaugc caaagagaau | 720 |
| gguaccaagc uguugcugac aaaugaucca uuggaagcag cgcauggagg caauguauua | 780 |
| auuacagaca cuuggauaag caugggacaa gaagaggaga agaaaaagcg gcuccaggcu | 840 |
| uuccaagguu accagguuac aaugaagacu gcuaaguugu cugccucuga cuggacauuu | 900 |
| uuacacugcu ugcccagaaa gccagaagaa guggaugaug aagucuuuua uucuccucga | 960 |
| ucacuagugu ucccagaggc agaaaacaga aaguggacaa ucauggcugu cauggugucc | 1020 |
| cugcugacag auuacucacc ucagcuccag aagccuaaau uuuga | 1065 |

<210> SEQ ID NO 2
<211> LENGTH: 1065
<212> TYPE: DNA
<213> ORGANISM: Artificial Sequence
<220> FEATURE:
<223> OTHER INFORMATION: Chemically synthesized nucleotide

<400> SEQUENCE: 2

| | |
|---|---|
| atgctgttta atctgaggat cctgttaaac aatgcagctt ttagaaatgg tcacaacttc | 60 |
| atggttcgaa attttcggtg tggacaacca ctacaaaata aagtgcagct gaagggccgt | 120 |
| gaccttctca ctctaaaaaa ctttaccgga aagaaatta aatatatgct atggctatca | 180 |
| gcagatctga aatttaggat aaaacagaaa ggagagtatt tgcctttatt gcaagggaag | 240 |
| tccttaggca tgattttga aaaagaagt actcgaacaa gattgtctac agaaacaggc | 300 |
| tttgcacttc tgggaggaca tccttgtttt cttaccacac aagatattca tttgggtgtg | 360 |
| aatgaaagtc tcacggacac ggcccgtgta ttgtctagca tggcagatgc agtattggct | 420 |
| cgagtgtata acaatcaga tttggacacc ctggctaaag aagcatccat cccaattatc | 480 |
| aatgggctgt cagatttgta ccatcctatc cagatcctgg ctgattacct cacgctccag | 540 |
| gaacactata gctctctgaa aggtcttacc ctcagctgga tcgggatgg gaacaatatc | 600 |
| ctgcactcca tcatgatgag cgcagcgaaa ttcggaatgc accttcaggc agctactcca | 660 |
| aagggttatg agccggatgc tagtgtaacc aagttggcag agcagtatgc caaagagaat | 720 |
| ggtaccaagc tgttgctgac aaatgatcca ttggaagcag cgcatggagg caatgtatta | 780 |
| attacagaca cttggataag catgggacaa gaagaggaga gaaaaagcg gctccaggct | 840 |
| ttccaaggtt accaggttac aatgaagact gctaagttg ctgcctctga ctggacattt | 900 |
| ttacactgct tgcccagaaa gccagaagaa gtggatgatg aagtctttta ttctcctcga | 960 |
| tcactagtgt tcccagaggc agaaaacaga agtggacaa tcatggctgt catggtgtcc | 1020 |
| ctgctgacag attactcacc tcagctccag aagcctaaat tttga | 1065 |

<210> SEQ ID NO 3
<211> LENGTH: 1065
<212> TYPE: RNA
<213> ORGANISM: Artificial Sequence
<220> FEATURE:
<223> OTHER INFORMATION: Chemically synthesized nucleotide

<400> SEQUENCE: 3

```
augcuguuca accuucggau cuugcugaac aacgcugcgu uccggaaugg ucacaacuuc      60
augguccgga acuucagaug cggccagccg cuccagaaca aggugcagcu caaggggagg     120
gaccuccuca cccugaaaaa cuucaccgga gaagagauca aguacaugcu guggcuguca     180
gccgaccuca aauuccggau caagcagaag ggcgaauacc uuccuuugcu gcagggaaag     240
ucccugggga ugaucuucga gaagcgcagc acucgcacua gacugucaac ugaaaccggc     300
uucgcgcugc uggaggaca ccccugcuuc cugaccaccc aagauaucca ucugggugug     360
aacgaauccc ucaccgacac agcgcggguu cugucgucca uggcagacgc gguccucgcc     420
cgcguguaca agcagucuga ucuggacacu cuggccaagg aagccuccau uccuaucauu     480
aauggauugu ccgaccucua ccaucccauc cagauucugg ccgauuaucu gacucugcaa     540
gaacauuaca gcucccugaa ggggcuuacc cuuucgugga ucggcgacgg caacaacauu     600
cugcacagca uuaugaugag cgcugccaag uuuggaaugc accuccaagc agcgaccccg     660
aagggauacg agccagacgc cuccgugacg aagcuggcug agcaguacgc caaggagaac     720
ggcacuaagc ugcugcucac caacgacccu cucgaagccg cccacgguggg caacgugcug     780
aucaccgaua ccuggaucuc caugggacag gaggaggaaa agaagaagcg ccugcaagca     840
uuucaggggu accaggugac uaugaaaacc gccaaggucg ccgccucgga cuggaccuuc     900
uugcacuguc ugcccagaaa gcccgaagag guggacgacg agguguucua cagcccgcgg     960
ucgcuggucu uuccggaggc cgaaaacagg aaguggacua ucauggccgu gaugguguccc    1020
cugcugaccg auuacuccccc gcagcugcag aaaccaaagu cuga                    1065
```

<210> SEQ ID NO 4
<211> LENGTH: 1310
<212> TYPE: RNA
<213> ORGANISM: Artificial Sequence
<220> FEATURE:
<223> OTHER INFORMATION: Chemically synthesized nucleotide

<400> SEQUENCE: 4

```
ggacagaucg ccuggagacg ccauccacgc uguuugacc uccauagaag acaccgggac       60
cgauccagcc uccgcggccg ggaacggugc auuggaacgc ggauucccg ugccaagagu      120
gacucaccgu ccuugacacg augcuguuua accugagaau ucugcugaac aacgccgcgu     180
ucaggaacgg ccacaauuuc augguccgca acuuuagaug cggacagccu cuccaaaaca     240
aguccagcu caaggggcgg gacuugcuga cccuuaagaa cuuuaccggc gaagagauca     300
aguacaugcu gugguuguca gcggaccuga aguuccgcau caagcagaaa ggggaguauc     360
ugccgcugcu ccaaggaaag ucgcucggca ugaucuucga gaagcgcucg accagaaccc     420
ggcuguccac ugaaacuggu uucgcccuuc uggguggaca cccuuguuuc cugacaaccc     480
aggacaucca ucugggcgug aacgaaagcc ucacugacac cgccagggug cugagcucca     540
uggccgacgc uguccuugcc cgggguguaca agcagcccga ucuggacacu cuggccaagg     600
aagcguccau cccgaucauu aacggacugu ccgaccugua ccacccgauc cagauucugg     660
```

-continued

```
ccgacuaccu gaccuugcaa gagcacuaca gcucacugaa gggcuugacc cugagcugga    720
ucggcgacgg aaacaacauu cugcauucga ucaugauguc cgcggccaag uucggaaugc    780
aucugcaggc cgcaacuccc aagggauacg aaccugaugc guccgugacu aagcuggccg    840
agcaguacgc aaaggaaaac ggcaccaagc ugcugcugac caacgacccg cucgaagcug    900
cccacggagg gaacgugcuc auuaccgaca cuuggaucuc caugggggcag gaagaagaga   960 agaagaagcg gcuccaggca uuccaggguu accaggucac caugaaaacg gccaaagugg   1020
ccgcuucgga uuggacuuuc cuccacugcc uuccccgcaa accugaggaa guggaugaug   1080
aaguguucua cuccccacgc ucccucgugu ucccgaggc cgagaaucgg aaguggacca   1140
uuauggccgu gauggugca cugcugaccg acuacagccc caacugcaa aagccgaagu    1200 ucugacgggu ggcaucccug ugaccccucc ccagugccuc uccuggcccu ggaaguugcc   1260
acuccagugc ccaccagccu uguccuaaua aaauuaaguu gcaucaagcu             1310
```

<210> SEQ ID NO 5
<211> LENGTH: 354
<212> TYPE: PRT
<213> ORGANISM: Homo sapiens

<400> SEQUENCE: 5

```
Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
```

```
              260                 265                 270
Glu Lys Lys Lys Arg Leu Gln Ala Phe Gln Gly Tyr Gln Val Thr Met
            275                 280                 285

Lys Thr Ala Lys Val Ala Ala Ser Asp Trp Thr Phe Leu His Cys Leu
        290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe

<210> SEQ ID NO 6
<211> LENGTH: 1065
<212> TYPE: RNA
<213> ORGANISM: Artificial Sequence
<220> FEATURE:
<223> OTHER INFORMATION: Chemically synthesized nucleotide

<400> SEQUENCE: 6
augcuuuuca accugagaau ucugcugaac aacgcagccu uccgcaacgg acacaacuuc      60
augguccgga acuucagaug cggacaaccg cugcagaaca agguccagcu caagggucgg     120
gaccuguuga cucuuaagaa uuucaccgga gaagaaauca aguacaugcu guggcuguuc     180
gccgaccuga aguuucgcau caagcagaag ggggaguacc uccccugcu gcaaggaaag      240 ucccugggaa ugauuuucga gaagcgcucc acccgcacua gacuuccac cgaaaccggc     300 uucgcucugc ugggcggaca uccuugcuuu cugacgacuc aggacaucca ccucggagug     360
aacgaauccc ucaccgauac cgccagggug cugagcagca uggccgacgc ugugcuggcu     420
cgggugacua agcaguccga ccucgacacc cuggccaagg aagccucgau cccuaucauc     480
aauggccugu cagaccugua ccacccaauc cagauucugg ccgacuaccu gacucuccaa     540
gagcacuaca gcagccucaa ggggcucaca uugccuugga ucggcgacgg caacaacauc     600
cuucacucca uuaugauguc ggccgccaaa ucgggaugc aucugcaggc agccacccu       660 aagggauacg agcccgaugc cucccugacc aagcucgccg aacagaugc gaaggagaac      720 ggcaccaagc uccugcucac uaacgauccg uuggaagcug cccacggcgg aaacgugcug     780
auuaccgaca ccuggaucag caugggcag gaagaagaga agaagaagcg gcugcaggcg     840 uuucagggu uaccaagucac caugaaaacu gccaaagucg cggcauccga cuggacuuuc     900
cugcacuguc ugccgaggaa accagaggaa guggaugacg aaguguucua cucacccggg     960 ucgcugguugu cccggaagc ggagaaccgg aaguggacca ucauggccgu gauggugucg    1020
cugcucaccg auuacucucc gcaacugcag aagcccaagu ucuga                    1065

<210> SEQ ID NO 7
<211> LENGTH: 1065
<212> TYPE: RNA
<213> ORGANISM: Artificial Sequence
<220> FEATURE:
<223> OTHER INFORMATION: Chemically synthesized nucleotide

<400> SEQUENCE: 7
augcuguuua accugagaau ucugcugaac aacgccgcgu ucaggaacgg ccacaauuuc      60
augguccgca acuuuagaug cggacagccu cuccaaaaca agguccagcu caaggggcgg     120
```

| | |
|---|---|
| gacuugcuga cccuuaagaa cuuuaccggc gaagagauca aguacaugcu gugguuguca | 180 |
| gcggaccuga aguuccgcau caagcagaaa ggggaguauc ugccgcugcu ccaaggaaag | 240 |
| ucgcucggca ugaucuucga gaagcgcucg accagaaccc ggcuguccac ugaaacuggu | 300 |
| uucgcccuuc uggguggaca cccuuguuuc cugacaaccc aggacaucca ucugggcgug | 360 |
| aacgaaagcc ucacugacac cgccagggug cugagcucca uggccgacgc uguccuugcc | 420 |
| cggguguaca agcagugcca ucuggacacu cuggccaagg aagcguccau cccgaucauu | 480 |
| aacggacugu ccgaccugua ccacccgauc cagauucugg ccgacuaccu gaccuugcaa | 540 |
| gagcacuaca gcucacugaa gggcuugacc cugagcugga ucggcgacgg aaacaacauu | 600 |
| cugcauucga ucaugaug uc cgcggccaag uucggaaugc aucugcaggc cgcaacuccc | 660 |
| aagggauacg aaccugaugc guccgugacu aagcuggccg agcaguacgc aaaggaaaac | 720 |
| ggcaccaagc ugcugcugac caacgacccg cucgaagcug cccacggagg gaacgugcuc | 780 |
| auuaccgaca cuuggaucuc caugggcag gaagaagaga gaagaagcg gcuccaggca | 840 |
| uccagggu accaggucac caugaaaacg gccaaagugg ccgcuucgga uuggacuuuc | 900 |
| cuccacugcc uucccgcaa accugaggaa guggaugaug aaguguucua cuccccacgc | 960 |
| ucccucgugu ucccgaggc cgagaaucgg aaguggacca uuauggccgu gauggugca | 1020 |
| cugcugaccg acuacagccc caacugcaa aagccgaagu ucuga | 1065 |

<210> SEQ ID NO 8
<211> LENGTH: 1065
<212> TYPE: RNA
<213> ORGANISM: Artificial Sequence
<220> FEATURE:
<223> OTHER INFORMATION: Chemically synthesized nucleotide

<400> SEQUENCE: 8

| | |
|---|---|
| augcuguuca accuccggau ccuccucaac aacgccgcgu uccgcaacgg ccacaacuuc | 60 |
| augguccgga auuccgaug cggacagcca cugcagaaca agguccagcu gaagggccgg | 120 |
| gacuugcuga cucucaagaa cuuuaccggg gaagaaauca aguacaugcu guggcuuucc | 180 |
| gccgaccuga aguucagaau caagcagaag ggcgaauauc uccccgcu gcaaggaaag | 240 |
| agccugggca ugauuucga gaagagaucg acacgcaccc ggcuguccac cgagacuggg | 300 |
| uuugcccugc uggagggaca cccguguuuc cugaccaccc aagauaucca ucucggagug | 360 |
| aacgaaucc uuacugacac ugcccgcgug uuguccucca uggcugaugc agugcucgcu | 420 |
| cggguguaca agcagagcga ccuggacacu cuggcgaagg aagcccucaau uccuaucauu | 480 |
| aacgggcugu cggaccugua ccacccgauc cagauucugg ccgacuaccu gacccugcaa | 540 |
| gaacacuacu caagccugaa gggucuuacc cugucccgga ucggcgacgg caacaacauc | 600 |
| cugcacucca ucaugauguc ggccgcgaag uucggaaugc accuccaagc agcgacuccg | 660 |
| aagggguuacg agccagaugc cuccgugacc aagcuggcgg agcaguacgc uaaggaaaac | 720 |
| ggaaccaagc ugcugcucac uaacgacccg uggaagccg cccaugugg aaaugugcug | 780 |
| aucacggaua ccuggaucag caugggccag gaggaagaga agaagaaaag gcuccaggcc | 840 |
| uuccaagggu accaggucac caugaaaacc gccaaagucg ccgcauccga uuggaccuuc | 900 |
| cuccacugcc ugcucggaa gccugaagag gucgacgacg aaguguucua cucccccgc | 960 |
| ucccuugugu ucccgaggc cgagaacagg aaguggacca uuauggccgu gaugguguccg | 1020 |
| cuccugaccg acuacagccc gcagcugcag aagcccaagu ucuga | 1065 |

<210> SEQ ID NO 9
<211> LENGTH: 1065
<212> TYPE: RNA
<213> ORGANISM: Artificial Sequence
<220> FEATURE:
<223> OTHER INFORMATION: Chemically synthesized nucleotide

<400> SEQUENCE: 9

```
augcuguuca aucuucggau ccugcugaac aacgccgccu uucggaacgg gcacaacuuc      60
augguccgca acuuccgcug uggacagccg cugcagaaca agguccagcu uaagggccgg     120
gaucuccuga cccugaagaa cuuuaccgga gaagaaauca aguacaugcu cuggcugagc     180
gccgaccuca aguccggau uaagcagaag ggggaguacc uccgcugcu caaggaaag      240
ucccugggga ugaucuucga gaagcggagc acuaggacca ggcugucgac cgaaacgggc     300
uuugcacugc uggguggaca cccaugcuuc cugaccaccc aagauauuca ucucggcgug     360
aacgaauccu ugacugacac ugcgcgcguc cucucaucga uggcugaugc cguguuggcu     420
agaguguaca agcagucaga ccuggacacu cuggcuaagg aagccuccau uccgaucauc     480
aacggccugu ccgaccugua cacccgauu cagauucugg ccgacuaccu gacccugcaa     540
gagcacuauu cgagccuuaa agguugacc cuguccugga ucggcgacgg aaacaauauc     600
uugcacucca uuaugaguc cgccgccaag uucggcaugc aucccaagc cgcgacuccu     660
aagguuacg agcccgacgc auccgugaca aaacuggccg agcaguacgc gaaggaaaac     720
gguaccaagc uccugcugac caugauccu cucgaggcug cgcacggagg aaacgugcuc     780
aucaccgaca ccuggaucag cauggacag gaagaggaaa agaaaaagcg ccugcaggca     840
uuccagggcu accaagucac uaugaaaacc gccaaagugg ccgccucgga uuggaccuuc     900
cuucacugcc ugccaagaaa gccugaggaa guggacgacg aaguguucua ucccccccgc     960
ucucucgugu ccccgaggc cgagaaccgg aaguggacca ucauggccgu gaugguguca    1020
cugcucacug acuacagccc gcagcugcag aagcccaagu ucuaa                    1065
```

<210> SEQ ID NO 10
<211> LENGTH: 1065
<212> TYPE: RNA
<213> ORGANISM: Artificial Sequence
<220> FEATURE:
<223> OTHER INFORMATION: Chemically synthesized nucleotide

<400> SEQUENCE: 10

```
augcuguuca accuccggau ucugcugaac aacgccgcuu uccgcaacgg ccacaauuuc      60
augguccgga acuucagaug cggccagccg uugcagaaca agguccagcu uaagggacgc     120
gaucugcuga cccugaagaa cuucaccgga gaggaaauca aguauaugcu guggcucucg     180
gccgaccuga aguucaggau caagcagaag ggggaguacc uccgcuguu gcaaggaaag     240
ucccugggca ugauuuucga gaagcgcuca acucgcacca ggcucuccac cgaaacuggu     300
uuugcccuuc ugggcgguca uccuugcuuu cugacgaccc aggacauuca ccucggagug     360
aaugagagcc ugaccgacac ugccagagug cuguccucca uggcggaugc aguguuggcg     420
cggguguaca agcagucaga ccuggacacc cuggcgaagg aagcgucaau ccccaucauu     480
aacggacuga gcgaccugua cacccgauc cagauccucg ccgacuaccu gacucuccaa     540
gaacacuacu cgucccugaa agggcugacc uugagcugga ucggcgacgg caacaacauc     600
cugcauucca ucaugaugag cgccgccaag uucggaaugc accuucaagc cgcaacaccg     660
aagggcuacg agccggaugc cucggugacc aagcuggccg agcaguacgc caaggaaaac     720
```

| | |
|---|---|
| gggaccaagc ugcugcucac uaacgacccu cuggaagcug cucacggggg aaacgugcug | 780 |
| aucaccgaca ccuggauuuc caugggacag gaagaagaga aaaagaagcg gcuucaggcg | 840 |
| uuccaggguu accaagucac caugaaaacc gccaaagugg cagccagcga cuggacuuuc | 900 |
| cugcauuguc ucccucggaa gccugaggaa guggaugacg aaguguuuua cucuccccgc | 960 |
| ucccuggugu uccccgaggc cgagaaccgg aaguggacua ucauggccgu gaugguguccc | 1020 |
| cuccugaccg auuacuccccc acaacugcag aagcccaagu ucuga | 1065 |

```
<210> SEQ ID NO 11
<211> LENGTH: 140
<212> TYPE: RNA
<213> ORGANISM: Artificial Sequence
<220> FEATURE:
<223> OTHER INFORMATION: Chemically synthesized nucleotide

<400> SEQUENCE: 11
```

| | |
|---|---|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg | 140 |

```
<210> SEQ ID NO 12
<211> LENGTH: 105
<212> TYPE: RNA
<213> ORGANISM: Artificial Sequence
<220> FEATURE:
<223> OTHER INFORMATION: Chemically synthesized nucleotide

<400> SEQUENCE: 12
```

| | |
|---|---|
| cggguggcau cccugugacc cuccccagu gccucuccug gcccuggaag uugccacucc | 60 |
| agugcccacc agccuugucc uaauaaaauu aaguugcauc aagcu | 105 |

```
<210> SEQ ID NO 13
<211> LENGTH: 105
<212> TYPE: RNA
<213> ORGANISM: Artificial Sequence
<220> FEATURE:
<223> OTHER INFORMATION: Chemically synthesized nucleotide

<400> SEQUENCE: 13
```

| | |
|---|---|
| ggguggcauc ccugugaccc uccccagug ccucuccugg cccuggaagu ugccacucca | 60 |
| gugcccacca gccuuguccu aauaaaauua aguugcauca aagcu | 105 |

```
<210> SEQ ID NO 14
<211> LENGTH: 1310
<212> TYPE: RNA
<213> ORGANISM: Artificial Sequence
<220> FEATURE:
<223> OTHER INFORMATION: Chemically synthesized nucleotide

<400> SEQUENCE: 14
```

| | |
|---|---|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg augcuguuca accuucggau cuugcugaac aacgcugcgu | 180 |
| uccggaaugg ucacaacuuc augguccgga acuucagaug cggccagccg cuccagaaca | 240 |
| aggugcagcu caaggggagg gaccuccuca cccugaaaaa cuucaccgga gaagagauca | 300 |
| aguacaugcu guggcuguca gccgaccuca aauuccggau caagcagaag ggcgaauacc | 360 |
| uuccuuugcu gcagggaaag ucccuggga ugaucuucga gaagcgcagc acucgcacua | 420 |

```
gacugucaac ugaaaccggc uucgcgcugc ugggaggaca ccccugcuuc cugaccaccc      480
aagauaucca ucuggguguq aacgaauccc ucaccgacac agcgcgggug cugucgucca      540
uggcagacgc gguccucgcc cgcguguaca agcagucuga ucuggacacu cuggccaagg      600
aagccuccau uccuaucauu aauggauugu ccgaccucua ccaucccauc cagauucugg      660
ccgauuaucu gacucugcaa gaacauuaca gcucccugaa ggggcuuacc cuucgcugga     720
ucggcgacgg caacaacauu cugcacagca uuaugaugag cgcugccaag uuggaaugc       780 accuccaagc agcgacccg aagggauacg agccagacgc cuccgugacg aagcuggcug      840
agcaguacgc caaggagaac ggcacuaagc ugcugcucac caacgacccu ucgaagccg      900 cccacggugg caacgugcug aucaccgaua ccuggaucuc caugggacag gaggaggaaa     960
agaagaagcg ccugcaagca uuucagggu accaggugac uaugaaaacc gccaaggucc     1020
ccgccucgga cuggaccuuc uugcacuguc ugcccagaaa gcccgaagag guggacgacg   1080 agguucua cagcccgcgg ucgcuggucu uccggaggc cgaaaacagg aaguggacua      1140
ucauggccgu gaugguguc cugcugaccg auuaucccc gcagcugcag aaaccaaagu     1200
ucugacgggu ggcaucccug ugacccccucc ccagugccuc uccuggcccu ggaaguugcc   1260
acuccagugc ccaccagccu uguccuaaua aaauuaaguu gcaucaagcu              1310
```

<210> SEQ ID NO 15
<211> LENGTH: 1310
<212> TYPE: RNA
<213> ORGANISM: Artificial Sequence
<220> FEATURE:
<223> OTHER INFORMATION: Chemically synthesized nucleotide

<400> SEQUENCE: 15

```
ggacagaucg ccuggagacg ccauccacgc uguuugacc uccauagaag acaccgggac      60
cgauccagcc uccgcggccg ggaacggugc auuggaacgc ggauucccg ugccaagagu    120 gacucaccgu ccuugacacg augcuguuca accuucggau cuugcugaac aacgcugcgu    180
uccggaaugg ucacaacuuc augguccgga acuucagaug cggccagccg cuccagaaca    240
aggugcagcu caagggagg gaccuccuca cccugaaaaa cuucaccgga gaagagauca     300
aguacaugcu guggcuguca gccgaccuca aauuccggau caagcagaag ggcgaauacc     360
uuccuuugcu gcagggaaag ucccugggga ugaucuucga gaagcgcagc acucgcacua    420
gacugucaac ugaaaccggc uucgcgcugc ugggaggaca ccccugcuuc cugaccaccc    480
aagauaucca ucuggguguq aacgaauccc ucaccgacac agcgcgggug cugucgucca    540
uggcagacgc gguccucgcc cgcguguaca agcagucuga ucuggacacu cuggccaagg    600
aagccuccau uccuaucauu aauggauugu ccgaccucua ccaucccauc cagauucugg    660
ccgauuaucu gacucugcaa gaacauuaca gcucccugaa ggggcuuacc cuucgcugga   720
ucggcgacgg caacaacauu cugcacagca uuaugaugag cgcugccaag uuggaaugc     780 accuccaagc agcgacccg aagggauacg agccagacgc cuccgugacg aagcuggcug    840
agcaguacgc caaggagaac ggcacuaagc ugcugcucac caacgacccu ucgaagccg    900 cccacggugg caacgugcug aucaccgaua ccuggaucuc caugggacag gaggaggaaa    960
```

-continued

```
agaagaagcg ccugcaagca uuucaggggu accaggugac uaugaaaacc gccaaggucg    1020
ccgccucgga cuggaccuuc uugcacuguc ugcccagaaa gcccgaagag guggacgacg    1080
agguguucua cagcccgcgg ucgcuggucu uuccggaggc cgaaacagg aaguggacua     1140 ucauggccgu gaugguguce cugcugaccg auuacucccc gcagcugcag aaaccaaagu    1200
ucugagggug gcaucccugu gaccccuccc cagugccucu ccuggcccug gaaguugcca    1260
cuccagugcc caccagccuu guccuaauaa aauuaaguug caucaaagcu               1310
```

MESSENGER RNA THERAPY FOR THE TREATMENT OF ORNITHINE TRANSCARBAMYLASE DEFICIENCY

RELATED APPLICATIONS

This application claims priority to U.S. Provisional Application Ser. No. 62/349,331, filed Jun. 13, 2016 and U.S. Provisional Application Ser. No. 62/509,568, filed May 22, 2017, the disclosures of which are hereby incorporated by reference.

SEQUENCE LISTING

The present specification makes reference to a Sequence Listing (submitted electronically as a .txt file named "SL_MRT-1243US" on Jun. 13, 2017. The .txt file was generated Jun. 13, 2017 and is 22,141 bytes in size. The entire contents of the Sequence Listing are herein incorporated by reference.

BACKGROUND

Ornithine transcarbamylase (OTC) deficiency is an X-linked genetic disorder characterized by mutations in the gene for OTC. Mutations in the OTC gene eliminate or reduce the ability of the OTC enzyme catalyze the synthesis of citrulline (in the liver and small intestine) from carbamyl phosphate and ornithine. As a result, excess nitrogen, in the form of ammonia, accumulates in the blood, and travels to the nervous system, resulting in the symptoms associated with OTC deficiency. Mutations that abolish OTC activity completely result in the severe, neonatal-onset form while mutations leading to decreased OTC activity result in the late-onset phenotypes.

OTC deficiency is the most common type of urea cycle disorder and the incidence of the disease is between approximately 1/56,500 and 1/77,000 live births. Males with the severe, neonatal-onset type are normal at birth but develop poor sucking, hypotonia and lethargy after a few days, rapidly progressing into somnolence and coma. Seizures and hyperventilation may also be present. If untreated, severe encephalopathy will develop with a high risk for death. Patients with a milder form can present at any age. In infants, symptoms can be induced when switching from breast milk to whole milk. In children and adults, environmental stressors (i.e. fasting, high protein diet, pregnancy and the postpartum period, intercurrent illness, surgery) can trigger episodes of hyperammonemic encephalopathy along with nausea, vomiting, headaches, erratic behavior, delirium and combativeness. These episodes can also result in hyperammonemic coma. Neurological complications of hyperammonemic coma include developmental delay and (sometimes) severe cognitive impairment. Many female carriers are asymptomatic; however they can be affected to the same extent as males if the degree of X-inactivation of the disease allele is unfavorable. Coagulopathy is a frequent finding during metabolic decompensation and sometimes evolves into acute liver failure.

Currently, there is no cure for OTC deficiency and long-term therapy involves life-long restriction of protein intake and nitrogen scavenger therapy (with sodium phenylacetate or sodium phenylbutyrate and/or sodium benzoate). Liver transplantation may also be considered in patients with severe, neonatal-onset OTC deficiency (usually performed by 6 months of age) or those with frequent hyperammonemic episodes.

SUMMARY OF THE INVENTION

The present invention provides, among other things, improved methods and compositions for the treatment of Ornithine transcarbamylase (OTC) deficiency based on mRNA therapy. The invention encompasses the observation that administration of an mRNA encoding a human OTC protein, encapsulated within a liposome, resulted in highly efficient and sustained protein production in vivo and successful reduction of, for example, orotic acid levels in urine, a clinically-relevant disease marker.

In one aspect, the present invention provides methods of treating ornithine transcarbamylase (OTC) deficiency, comprising administering to a subject in need of treatment a composition comprising an mRNA encoding an ornithine transcarbyamylase (OTC) protein at an effective dose and an administration interval such that at least one symptom or feature of the OTC deficiency is reduced in intensity, severity, or frequency or has delayed onset. In some embodiments, the mRNA encoding the OTC protein is codon optimized. In some embodiments, the mRNA encoding the OTC protein comprises a polynucleotide sequence at least 70%, 75%, 80%, 85%, 90%, or 95% identical to SEQ ID NO: 3, SEQ ID NO: 6, SEQ ID NO: 7, SEQ ID NO: 8, SEQ ID NO: 9 or SEQ ID NO: 10. In some embodiments, the mRNA encoding the OTC protein comprises SEQ ID NO: 3. In some embodiments, the mRNA encoding the OTC protein comprises SEQ ID NO: 6. In some embodiments, the mRNA encoding the OTC protein comprises SEQ ID NO: 7. In some embodiments, the mRNA encoding the OTC protein comprises SEQ ID NO: 8. In some embodiments, the mRNA encoding the OTC protein comprises SEQ ID NO: 9. In some embodiments, the mRNA encoding the OTC protein comprises SEQ ID NO: 10. In some embodiments, the mRNA encoding the OTC protein is not SEQ ID NO: 1.

In some embodiments, the mRNA further comprises the 5' untranslated region (UTR) sequence of SEQ ID NO: 11. In some embodiments, the mRNA further comprises the 3' untranslated region (UTR) sequence of SEQ ID NO: 12 or SEQ ID NO: 13.

In some embodiments, the mRNA is encapsulated within a liposome. In some embodiments, the liposome comprises one or more cationic lipids, one or more non-cationic lipids, one or more cholesterol-based lipids and one or more PEG-modified lipids. In some embodiments, the one or more cationic lipids comprise a cationic lipid selected from the group consisting of C12-200, MC3, DLinDMA, DLinkC2DMA, cKK-E12, ICE (Imidazole-based), HGT5000, HGT5001, OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof. In some embodiments, the one or more non-cationic lipids are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)) and combinations thereof. In some embodiments, the one or more cholesterol-based lipids are cholesterol and/or PEGylated cholesterol.

In some embodiments, the liposome has a size less than about 100 nm.

In some embodiments, the mRNA is administered at the effective dose ranging from about 0.01-5.0 mg/kg body weight. In some embodiments, the mRNA is administered at the effective dose ranging from about 0.01-3.0 mg/kg body weight. In some embodiments, the mRNA is administered at the effective dose ranging from about 0.01-1.0 mg/kg body weight. In some embodiments, the mRNA is administered at the effective dose ranging from about 0.01-0.5 mg/kg body weight.

In some embodiments, the composition is administered intravenously. In some embodiments, the composition is administered once a week. In some embodiments, the composition is administered twice a month. In some embodiments, the composition is administered once every 14 days. In some embodiments, the composition is administered once a month.

In some embodiments, the administering of the composition results in an increased OTC protein expression or activity level in serum of the subject as compared to a control level. In some embodiments, the control level is a baseline serum OTC protein expression or activity level in the subject prior to the treatment. In some embodiments, the control level is a reference level indicative of the average serum OTC protein expression or activity level in OTC patients without treatment. In some embodiments, the administering of the composition results in a reduced urinary orotic acid level in the subject as compared to a control orotic acid level. In some embodiments, the control orotic acid level is a baseline urinary orotic acid level in the subject prior to the treatment. In some embodiments, the control orotic acid level is a reference level indicative of the average urinary orotic acid level in OTC patients without treatment. In some embodiments, wherein the administering of the composition results in an increased citrulline level in serum of the subject as compared to a control citrulline level. In some embodiments, the control citrulline level is a baseline serum citrulline level in the subject prior to the treatment. In some embodiments, the control citrulline level is a reference level indicative of the average serum citrulline level in OTC patients without treatment.

In some embodiments, the mRNA comprises one or more modified nucleotides. In some embodiments, the one or more modified nucleotides comprise pseudouridine, N-1-methyl-pseudouridine, 2-aminoadenosine, 2-thiothymidine, inosine, pyrrolo-pyrimidine, 3-methyl adenosine, 5-methyl-cytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

In some embodiments, the mRNA is unmodified.

In one aspect, the present invention provides pharmaceutical compositions for treating ornithine transcarbamylase (OTC) deficiency, comprising an mRNA encoding an ornithine transcarbyamylase (OTC) protein and wherein the mRNA encoding the OTC protein comprises a polynucleotide sequence at least 70%, 75%, 80%, 85%, 90%, or 95% identical to SEQ ID NO: 3, SEQ ID NO: 6, SEQ ID NO: 7, SEQ ID NO: 8, SEQ ID NO: 9 or SEQ ID NO: 10.

In some embodiments, the mRNA encoding the OTC protein comprises SEQ ID NO: 3. In some embodiments, the mRNA encoding the OTC protein comprises SEQ ID NO: 6. In some embodiments, the mRNA encoding the OTC protein comprises SEQ ID NO: 7. In some embodiments, the mRNA encoding the OTC protein comprises SEQ ID NO: 8. In some embodiments, the mRNA encoding the OTC protein comprises SEQ ID NO: 9. In some embodiments, the mRNA encoding the OTC protein comprises SEQ ID NO: 10. In some embodiments, the mRNA encoding the OTC protein is not SEQ ID NO: 1. In some embodiments, the mRNA further comprises the 5' untranslated region (UTR) sequence of SEQ ID NO: 11. In some embodiments, the mRNA further comprises the 3' untranslated region (UTR) sequence of SEQ ID NO: 12 or SEQ ID NO: 13.

In some embodiments, the mRNA encoding the OTC protein is encapsulated within a liposome. In some embodiments, the liposome comprises one or more cationic lipids, one or more non-cationic lipids, one or more cholesterol-based lipids and one or more PEG-modified lipids. In some embodiments, the liposome has a size less than about 100 nm.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

DEFINITIONS

Figure 1:
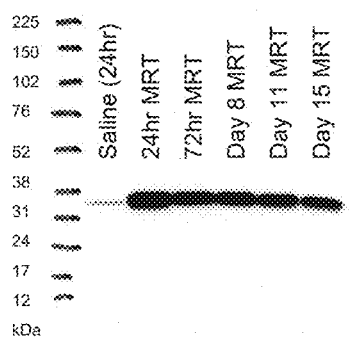
FIG. 1 depicts exemplary immunohistochemical detection of human OTC protein by Western blot over a two-week period after a single 0.5 mg/kg dose of hOTC mRNA-loaded lipid nanoparticles.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("$C_{1-15}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$), n-dodecyl ($C_{12}$) and the like. The prefix "n-" (normal) refers to unbranched alkyl groups. For example, n-$C_8$ alkyl refers to —$(CH_2)_7CH_3$, n-$C_{10}$ alkyl refers to —$(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery").

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polyribonucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, in vitro transcribed, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quaternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods and compositions for treating ornithine transcarbamylase (OTC) deficiency based on mRNA therapy. In particular, the present invention provides methods for treating OTC deficiency by administering to a subject in need of treatment a composition comprising an mRNA encoding ornithine transcarbamylase (OTC) at an effective dose and an administration interval such that at least one symptom or feature of OTC deficiency is reduced in intensity, severity, or frequency or has a delayed onset. The present invention further provides methods of treating OTC deficiency comprising administering to a subject in need of treatment a therapeutically effective amount of a composition comprising an mRNA encoding acid OTC such that hyperammonemia in the subject is treated. In some embodiments, the mRNA is encapsulated within one or more liposomes. As used herein, the term "liposome" refers to any lamellar, multilamellar, or solid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In some embodiments, a liposome suitable for the present invention contains cationic or non-cationic lipid(s), cholesterol-based lipid(s) and PEG-modified lipid(s).

Ornithine Transcarbamylase (OTC) Deficiency

The present invention may be used to treat a subject who is suffering from or susceptible to ornithine transcarbamylase (OTC) deficiency. OTC deficiency is an X-linked genetic disorder characterized by mutations in the gene for the enzyme ornithine transcarbamylase (OTC). The OTC enzyme is also known as ornithine carbamoyltransferase, mitochondrial. The OTC gene is also known as: MGC129967, MGC129968, OCTD, ornithine carbamoyltransferase precursor, ornithine transcarbamylase, and OTC_HUMAN. More than 300 mutations that cause OTC deficiency have been identified in the OTC gene. Many of the mutations in the OTC gene likely affect the structure of the resulting protein and decrease its activity.

Compositions and methods described herein may be used to treat at least one symptom or feature of OTC deficiency. In particular, the compositions and methods described herein may be used to treat hyperammonemia.

Mutations in the OTC gene eliminate or reduce the ability of the OTC enzyme catalyze the synthesis of citrulline (in the liver and small intestine) from carbamyl phosphate and ornithine. As a result, excess nitrogen, in the form of ammonia, accumulates in the blood, and travels to the nervous system, resulting in the symptoms associated with OTC deficiency. The accumulation of ammonia can lead to brain damage and death. Mutations that abolish OTC activity completely result in the severe, neonatal-onset form while mutations leading to decreased OTC activity result in the late-onset phenotypes.

Ornithine Transcarbamylase (OTC)

In some embodiments, the present invention provides methods and compositions for delivering mRNA encoding OTC to a subject for the treatment of OTC deficiency. A suitable OTC mRNA encodes any full length, fragment or portion of an OTC protein which can be substituted for naturally-occurring OTC protein activity and/or reduce the intensity, severity, and/or frequency of one or more symptoms associated with OTC deficiency.

In some embodiments, a suitable mRNA sequence is an mRNA sequence encoding a human OTC protein. The naturally-occurring human OTC mRNA coding sequence and the corresponding amino acid sequence are shown in Table 1:

TABLE 1

Human OTC

| | |
|---|---|
| Human OTC (mRNA coding sequence) | (SEQ ID NO: 1)<br>AUGCUGUUUAAUCUGAGGAUCCUGUUAAACAAUGCAGCUUUUAGAAA<br>UGGUCACAACUUCAUGGUUCGAAAUUUUCGGUGUGGACAACCACUAC<br>AAAAUAAAGUGCAGCUGAAGGGCCGUGACCUUCUCACUCUAAAAAAC<br>UUUACCGGAGAAGAAAUUAAAUAUAUGCUAUGGCUAUCAGCAGAUCU<br>GAAAUUUAGGAUAAAACAGAAAGGAGAGUAUUUGCCUUUAUUGCAAG<br>GGAAGUCCUUAGGCAUGAUUUUUGAGAAAAGAAGUACUCGAACAAGA<br>UUGUCUACAGAAACAGGCUUUGCACUUCUGGGAGGACAUCCUUGUUU<br>UCUUACCACACAAGAUAUUCAUUUGGGUGUGAAUGAAAGUCUCACGG<br>ACACGGCCCGUGUAUUGUCUAGCAUGGCAGAUGCAGUAUUGGCUCGA<br>GUGUAUAAACAAUCAGAUUUGGACACCCUGGCUAAAGAAGCAUCCAU<br>CCCAAUUAUCAAUGGGCUGUCAGAUUUGUACCAUCCUAUCCAGAUCCU<br>GGCUGAUUACCUCACGCUCCAGGAACACUAUAGCUCUCUGAAAGGUCU<br>UACCCUCAGCUGGAUCGGGGAUGGGAACAAUAUCCUGCACUCCAUCAU<br>GAUGAGCGCAGCGAAAUUCGGAAUGCACCUUCAGGCAGCUACUCCAAA<br>GGGUUAUGAGCCGGAUGCUAGUGUAACCAAGUUGGCAGAGCAGUAUG<br>CCAAAGAGAAUGGUACCAAGCUGUUGCUGACAAAUGAUCCAUUGGAA<br>GCAGCGCAUGGAGGCAAUGUAUUAAUUACAGACACUUGGAUAAGCAU<br>GGGACAAGAAGAGGAGAAGAAAAAGCGGCUCCAGGCUUUCCAAGGUU<br>ACCAGGUUACAAUGAAGACUGCUAAAGUUGCUGCCUCUGACUGGACA<br>UUUUUACACUGCUUGCCCAGAAAGCCAGAAGAAGUGGAUGAUGAAGU<br>CUUUUAUUCUCCUCGAUCACUAGUGUUCCCAGAGGCAGAAAACAGAA<br>AGUGGACAAUCAUGGCUGUCAUGGUGUCCCUGCUGACAGAUUACUCA<br>CCUCAGCUCCAGAAGCCUAAAUUUUGA |
| Human OTC (DNA Sequence) | (SEQ ID NO: 2)<br>ATGCTGTTTAATCTGAGGATCCTGTTAAACAATGCAGCTTTTAGAAATGG<br>TCACAACTTCATGGTTCGAAATTTTCGGTGTGGACAACCACTACAAAATA<br>AAGTGCAGCTGAAGGGCCGTGACCTTCTCACTCTAAAAAACTTTACCGG<br>AGAAGAAATTAAATATATGCTATGGCTATCAGCAGATCTGAAATTTAGG<br>ATAAAACAGAAAGGAGAGTATTTGCCTTTATTGCAAGGGAAGTCCTTAG<br>GCATGATTTTTGAGAAAAGAAGTACTCGAACAAGATTGTCTACAGAAAC<br>AGGCTTTGCACTTCTGGGAGGACATCCTTGTTTTCTTACCACACAAGATA<br>TTCATTTGGGTGTGAATGAAAGTCTCACGGACACGGCCCGTGTATTGTCT<br>AGCATGGCAGATGCAGTATTGGCTCGAGTGTATAAACAATCAGATTTGG<br>ACACCCTGGCTAAAGAAGCATCCATCCCAATTATCAATGGGCTGTCAGA<br>TTTGTACCATCCTATCCAGATCCTGGCTGATTACCTCACGCTCCAGGAAC<br>ACTATAGCTCTCTGAAAGGTCTTACCCTCAGCTGGATCGGGGATGGGAA<br>CAATATCCTGCACTCCATCATGATGAGCGCAGCGAAATTCGGAATGCAC<br>CTTCAGGCAGCTACTCCAAAGGGTTATGAGCCGGATGCTAGTGTAACCA<br>AGTTGGCAGAGCAGTATGCCAAAGAGAATGGTACCAAGCTGTTGCTGAC<br>AAATGATCCATTGGAAGCAGCGCATGGAGGCAATGTATTAATTACAGAC<br>ACTTGGATAAGCATGGGACAAGAAGAGGAGAAGAAAAAGCGGCTCCAG<br>GCTTTCCAAGGTTACCAGGTTACAATGAAGACTGCTAAAGTTGCTGCCTC<br>TGACTGGACATTTTTACACTGCTTGCCCAGAAAGCCAGAAGAAGTGGAT<br>GATGAAGTCTTTTATTCTCCTCGATCACTAGTGTTCCCAGAGGCAGAAAA<br>CAGAAAGTGGACAATCATGGCTGTCATGGTGTCCCTGCTGACAGATTAC<br>TCACCTCAGCTCCAGAAGCCTAAATTTTGA |
| Human OTC Protein Sequence | (SEQ ID NO: 5)<br>MLFNLRILLNNAAFRNGHNFMVRNFRCGQPLQNKVQLKGRDLLTLKNFTG<br>EEIKYMLWLSADLKFRIKQKGEYLPLLQGKSLGMIFEKRSTRTRLSTETGFA<br>LLGGHPCFLTTQDIHLGVNESLTDTARVLSSMADAVLARVYKQSDLDTLAK<br>EASIPIINGLSDLYHPIQILADYLTLQEHYSSLKGLTLSWIGDGNNILHSIMMS<br>AAKFGMHLQAATPKGYEPDASVTKLAEQYAKENGTKLLLTNDPLEAAHGG<br>NVLITDTWISMGQEEEKKKRLQAFQGYQVTMKTAKVAASDWTFLHCLPRK<br>PEEVDDEVFYSPRSLVFPEAENRKWTIMAVMVSLLTDYSPQLQKPKF |

In some embodiments, a suitable mRNA is a wild-type human OTC mRNA of sequence (SEQ ID NO: 1). In some embodiments, a suitable mRNA may be a codon optimized hOTC sequence. In some embodiments, a suitable codon optimized mRNA can encode an OTC amino acid sequence shown in Table 1 as SEQ ID NO: 5 or an amino acid sequence at least 70%, 75%, 80%, 85%, 90%, 95%, 96%, 97%, 98%, or 99% identical to SEQ ID NO: 5. Exemplary suitable codon optimized mRNA sequences are described below.

In some embodiments, a suitable mRNA may be a codon optimized sequence as shown in SEQ ID NO: 3:

```
                                                    (SEQ ID NO: 3)
AUGCUGUUCAACCUUCGGAUCUUGCUGAACAACGCUGCGUUCCGGAAUGG

UCACAACUUCAUGGUCCGGAACUUCAGAUGCGGCCAGCCGCUCCAGAACA

AGGUGCAGCUCAAGGGGAGGGACCUCCUCACCCUGAAAAACUUCACCGGA

GAAGAGAUCAAGUACAUGCUGUGGCUGUCAGCCGACCUCAAAUUCCGGAU

CAAGCAGAAGGGCGAAUACCUUCCUUUGCUGCAGGGAAAGUCCCUGGGGA

UGAUCUUCGAGAAGCGCAGCACUCGCACUAGACUGUCAACUGAAACCGGC

UUCGCGCUGCUGGGAGGACACCCCUGCUUCCUGACCACCCAAGAUAUCCA

UCUGGGUGUGAACGAAUCCCUCACCGACACAGCGCGGGUGCUGUCGUCCA

UGGCAGACGCGGUCCUCGCCCGCGUGUACAAGCAGUCUGAUCUGGACACU

CUGGCCAAGGAAGCCUCCAUUCCUAUCAUUAAUGGAUUGUCCGACCUCUA

CCAUCCCAUCCAGAUUCUGGCCGAUUAUCUGACUCUGCAAGAACAUUACA

GCUCCCUGAAGGGGCUUACCCUUUCGUGGAUCGGCGACGGCAACAACAUU

CUGCACAGCAUUAUGAUGAGCGCUGCCAAGUUUGGAAUGCACCUCCAAGC

AGCGACCCCGAAGGGAUACGAGCCAGACGCCUCCGUGACGAAGCUGGCUG

AGCAGUACGCCAAGGAGAACGGCACUAAGCUGCUGCUCACCAACGACCCU

CUCGAAGCCGCCCACGGUGGCAACGUGCUGAUCACCGAUACCUGGAUCUC

CAUGGGACAGGAGGAGGAAAAGAAGAAGCGCCUGCAAGCAUUUCAGGGGU

ACCAGGUGACUAUGAAAACCGCCAAGGUCGCCGCCUCGGACUGGACCUUC

UUGCACUGUCUGCCCAGAAAGCCCGAAGAGGUGGACGACGAGGUGUUCUA

CAGCCCGCGGUCGCUGGUCUUUCCGGAGGCCGAAAACAGGAAGUGGACUA

UCAUGGCCGUGAUGGUGUCCCUGCUGACCGAUUACUCCCCGCAGCUGCAG

AAACCAAAGUUCUGA
```

In some embodiments, a suitable mRNA may be a codon optimized sequence as shown in SEQ ID NO: 6.

```
                                                    (SEQ ID NO: 6)
AUGCUUUUCAACCUGAGAAUUCUGCUGAACAACGCAGCCUUCCGCAACGG

ACACAACUUCAUGGUCCGGAACUUCAGAUGCGGACAACCGCUGCAGAACA

AGGUCCAGCUCAAGGGUCGGGACCUGUUGACUCUUAAGAAUUUCACCGGA

GAAGAAAUCAAGUACAUGCUGUGGCUGUCCGCCGACCUGAAGUUUCGCAU

CAAGCAGAAGGGGGAGUACCUCCCCCUGCUGCAAGGAAAGUCCCUGGGAA

UGAUUUUCGAGAAGCGCUCCACCCGCACUAGACUUUCCACCGAAACCGGC

UUCGCUCUGCUGGGCGGACAUCCUUGCUUUCUGACGACUCAGGACAUCCA

CCUCGGAGUGAACGAAUCCCUCACCGAUACCGCCAGGGUGCUGAGCAGCA

UGGCCGACGCUGUGCUGGCUCGGGUGUACAAGCAGUCCGACCUCGACACC

CUGGCCAAGGAAGCCUCGAUCCCUAUCAUCAAUGGCCUGUCAGACCUGUA

CCACCCAAUCCAGAUUCUGGCCGACUACCUGACUCUCCAAGAGCACUACA

GCAGCCUCAAGGGGCUCACAUUGUCCUGGAUCGGCGACGGCAACAACAUC

CUUCACUCCAUUAUGAUGUCGGCCGCAAAUUCGGGAUGCAUCUGCAGGC

AGCCACCCCUAAGGGAUACGAGCCCGAUGCCUCCGUGACCAAGCUCGCCG

AACAGUAUGCGAAGGAGAACGGCACCAAGCUCCUGCUCACUAACGAUCCG

UUGGAAGCUGCCCACGGCGGAAACGUGCUGAUUACCGACACCUGGAUCAG

CAUGGGGCAGGAAGAAGAGAAGAAGAAGCGGCUGCAGGCGUUUCAGGGUU

ACCAAGUCACCAUGAAAACUGCCAAAGUCGCGGCAUCCGACUGGACUUUC

CUGCACUGUCUGCCGAGGAAACCAGAGGAAGUGGAUGACGAAGUGUUCUA

CUCACCCCGGUCGCUGGUGUUCCCGGAAGCGGAGAACCGGAAGUGGACCA

UCAUGGCCGUGAUGGUGUCGCUGCUCACCGAUUACUCUCCGCAACUGCAG

AAGCCCAAGUUCUGA
```

In some embodiments, a suitable mRNA may be a codon optimized sequence as shown in SEQ ID NO: 7.

```
                                                    (SEQ ID NO: 7)
AUGCUGUUUAACCUGAGAAUUCUGCUGAACAACGCCGCGUUCAGGAACGG

CCACAAUUUCAUGGUCCGCAACUUUAGAUGCGGACAGCCUCUCCAAAACA

AGGUCCAGCUCAAGGGGCGGGACUUGCUGACCCUUAAGAACUUUACCGGC

GAAGAGAUCAAGUACAUGCUGUGGUUGUCAGCGGACCUGAAGUUCCGCAU

CAAGCAGAAAGGGGAGUAUCUGCCGCUGCUCCAAGGAAAGUCGCUCGGCA

UGAUCUUCGAGAAGCGCUCGACCAGAACCCGGCUGUCCACUGAAACUGGU

UUCGCCCUUCUGGGGUGGACACCCUUGUUUCCUGACAACCCAGGACAUCCA

UCUGGGCGUGAACGAAAGCCUCACUGACACCGCCAGGGUGCUGAGCUCCA

UGGCCGACGCUGUCCUUGCCCGGGUGUACAAGCAGUCCGAUCUGGACACU

CUGGCCAAGGAAGCGUCCAUCCCGAUCAUUAACGGACUGUCCGACCUGUA

CCACCCGAUCCAGAUUCUGGCCGACUACCUGACCUUGCAAGAGCACUACA

GCUCACUGAAGGGCUUGACCCUGAGCUGGAUCGGCGACGGAAACAACAUU

CUGCAUUCGAUCAUGAUGUCCGCGGCCAAGUUCGGAAUGCAUCUGCAGGC

CGCAACUCCCAAGGGAUACGAACCUGAUGCGUCCGUGACUAAGCUGGCCG

AGCAGUACGCAAAGGAAAACGGCACCAAGCUGCUGCUGACCAACGACCCG

CUCGAAGCUGCCCACGGAGGGAACGUGCUCAUUACCGACACUUGGAUCUC

CAUGGGGCAGGAAGAAGAGAAGAAGAAGCGGCUCCAGGCAUUCCAGGGUU

ACCAGGUCACCAUGAAAACGGCCAAAGUGGCCGCUUCGGAUUGGACUUUC

CUCCACUGCCUUCCCGCAAACCUGAGGAAGUGGAUGAUGAAGUGUUCUA

CUCCCCACGCUCCCUCGUGUUCCCCGAGGCCGAGAAUCGGAAGUGGACCA

UUAUGGCCGUGAUGGUGUCACUGCUGACCGACUACAGCCCCCAACUGCAA

AAGCCGAAGUUCUGA
```

In some embodiments, a suitable mRNA may be a codon optimized sequence as shown in SEQ ID NO: 8.

(SEQ ID NO: 8)
AUGCUGUUCAACCUCCGGAUCCUCCUCAACAACGCCGCGUUCCGCAACGG

CCACAACUUCAUGGUCCGGAAUUUCCGAUGCGGACAGCCACUGCAGAACA

AGGUCCAGCUGAAGGGCCGGGACUUGCUGACUCUCAAGAACUUUACCGGG

GAAGAAAUCAAGUACAUGCUGUGGCUUUCCGCCGACCUGAAGUUCAGAAU

CAAGCAGAAGGGCGAAUAUCUCCCCCUGCUGCAAGGAAAGAGCCUGGGCA

UGAUUUUCGAGAAGAGAUCGACACGCACCCGGCUGUCCACCGAGACUGGG

UUUGCCCUGCUGGGAGGACACCCGUGUUUCCUGACCACCCAAGAUAUCCA

UCUCGGAGUGAACGAAUCCCUUACUGACACUGCCCGCGUGUUGUCCUCCA

UGGCUGAUGCAGUGCUCGCUCGGGUGUACAAGCAGAGCGACCUGGACACU

CUGGCGAAGGAAGCCUCAAUUCCUAUCAUUAACGGGCUGUCGGACCUGUA

CCACCCGAUCCAGAUUCUGGCCGACUACCUGACCCUGCAAGAACACUACU

CAAGCCUGAAGGGUCUUACCCUGUCCUGGAUCGGCGACGGCAACAACAUC

CUGCACUCCAUCAUGAUGUCGGCCGCGAAGUUCGGAAUGCACCUCCAAGC

AGCGACUCCGAAGGGUUACGAGCCAGAUGCCUCCGUGACCAAGCUGGCGG

AGCAGUACGCUAAGGAAAACGGAACCAAGCUGCUGCUCACUAACGACCCG

UUGGAAGCCGCCCAUGGUGGAAAUGUGCUGAUCACGGAUACCUGGAUCAG

CAUGGGCCAGGAGGAAGAGAAGAAGAAAAGGCUCCAGGCCUUCCAAGGGU

ACCAGGUCACCAUGAAAACCGCCAAAGUCGCCGCAUCCGAUUGGACCUUC

CUCCACUGCCUGCCUCGGAAGCCUGAAGAGGUCGACGACGAAGUGUUCUA

CUCUCCCCGCUCCCUUGUGUUCCCCGAGGCCGAGAACAGGAAGUGGACCA

UUAUGGCCGUGAUGGUGUCGCUCCUGACCGACUACAGCCCGCAGCUGCAG

AAGCCCAAGUUCUGA

In some embodiments, a suitable mRNA may be a codon optimized sequence as shown in SEQ ID NO: 9.

(SEQ ID NO: 9)
AUGCUGUUCAAUCUUCGGAUCCUGCUGAACAACGCCGCCUUUCGGAACGG

GCACAACUUCAUGGUCCGCAACUUCCGCUGUGGACAGCCGCUGCAGAACA

AGGUCCAGCUUAAGGGCCGGGAUCUCCUGACCCUGAAGAACUUUACCGGA

GAAGAAAUCAAGUACAUGCUCUGGCUGAGCGCCGACCUCAAGUUCCGGAU

UAAGCAGAAGGGGGAGUACCUCCCGCUGCUUCAAGGAAAGUCCCUGGGA

UGAUCUUCGAGAAGCGGAGCACUAGGACCAGGCUGUCGACCGAAACGGGC

UUUGCACUGCUGGGUGGACACCCAUGCUUCCUGACCACCCAAGAUAUUCA

UCUCGGCGUGAACGAAUCCUUGACUGACACUGCGCGCGUCCUCUCAUCGA

UGGCUGAUGCCGUGUUGGCUAGAGUGUACAAGCAGUCAGACCUGGACACU

CUGGCUAAGGAAGCCUCCAUUCCGAUCAUCAACGGCCUGUCCGACCUGUA

CCACCCGAUUCAGAUUCUGGCCGACUACCUGACCCUGCAAGAGCACUAUU

CGAGCCUUAAAGGGUUGACCCUGUCCUGGAUCGGCGACGAAACAAUAUC

UUGCACUCCAUUAUGAUGUCCGCCGCCAAGUUCGGCAUGCAUCUCCAAGC

CGCGACUCCUAAGGGUUACGAGCCCGACGCAUCCGUGACAAAACUGGCCG

AGCAGUACGCGAAGGAAAACGGUACCAAGCUCCUGCUGACCAAUGAUCCU

CUCGAGGCUGCGCACGGAGGAAACGUGCUCAUCACCGACACCUGGAUCAG

CAUGGGACAGGAAGAGGAAAAAGAAAAAGCGCCUGCAGGCAUUCCAGGGCU

ACCAAGUCACUAUGAAAACCGCCAAAGUGGCCGCCUCGGAUUGGACCUUC

CUUCACUGCCUGCCAAGAAAGCCUGAGGAAGUGGACGACGAAGUGUUCUA

CUCCCCCCGCUCUCUCGUGUUCCCCGAGGCCGAGAACCGGAAGUGGACCA

UCAUGGCCGUGAUGGUGUCACUGCUCACUGACUACAGCCCGCAGCUGCAG

AAGCCCAAGUUCUAA

In some embodiments, a suitable mRNA may be a codon optimized sequence as shown in SEQ ID NO: 10.

(SEQ ID NO: 10)
AUGCUGUUCAACCUCCGGAUUCUGCUGAACAACGCCGCUUUCCGCAACGG

CCACAAUUUCAUGGUCCGGAACUUCAGAUGCGGCCAGCCGUUGCAGAACA

AGGUCCAGCUUAAGGGACGCGAUCUGCUGACCCUGAAGAACUUCACCGGA

GAGGAAAUCAAGUAUAUGCUGUGGCUCUCGGCCGACCUGAAGUUCAGGAU

CAAGCAGAAGGGGGAGUACCUCCCGCUGUUGCAAGGAAAGUCCCUGGGCA

UGAUUUUCGAGAAGCGCUCAACUCGCACCAGGCUCUCCACCGAAACUGGU

UUUGCCCUUCUGGGCGGUCAUCCUUGCUUUCUGACGACCCAGGACAUUCA

CCUCGGAGUGAAUGAGAGCCUGACCGACACUGCCAGAGUGCUGUCCUCCA

UGGCGGAUGCAGUGUUGGCGCGGGUGUACAAGCAGUCAGACCUGGACACC

CUGGCGAAGGAAGCGUCAAUCCCCAUCAUUAACGGACUGAGCGACCUGUA

CCACCCGAUCCAGAUCCUCGCCGACUACCUGACUCUCCAAGAACACUACU

CGUCCCUGAAAGGGCUGACCUUGAGCUGGAUCGGCGACGGCAACAACAUC

CUGCAUUCCAUCAUGAUGAGCGCCGCCAAGUUCGGAAUGCACCUUCAAGC

CGCAACACCGAAGGGCUACGAGCCGGAUGCCUCGGUGACCAAGCUGGCCG

AGCAGUACGCCAAGGAAAACGGGACCAAGCUGCUGCUCACUAACGACCCU

CUGGAAGCUGCUCACGGGGGAAACGUGCUGAUCACCGACACCUGGAUUUC

CAUGGGACAGGAAGAAGAGAAAAAGAAGCGGCUUCAGGCGUUCCAGGGUU

ACCAAGUCACCAUGAAAACCGCCAAAGUGGCAGCCAGCGACUGGACUUUC

CUGCAUUGUCUCCCUCGGAAGCCUGAGGAAGUGGAUGACGAAGUGUUUUA

CUCUCCCCGCUCCCUGGUGUUCCCCGAGGCCGAGAACCGGAAGUGGACUA

UCAUGGCCGUGAUGGUGUCCCUCCUGACCGAUUACUCCCCACAACUGCAG

AAGCCCAAGUUCUGA

Additional exemplary mRNA sequences are described in the Examples section below, for example, SEQ ID NO: 4, SEQ ID NO: 14 and SEQ ID NO: 15, all of which include 5' and 3' untranslated regions framing codon-optimized OTC-encoding mRNA.

In some embodiments, a suitable mRNA sequence may be an mRNA sequence a homolog or an analog of human OTC protein. For example, a homolog or an analog of human OTC protein may be a modified human OTC protein containing one or more amino acid substitutions, deletions, and/or insertions as compared to a wild-type or naturally-occurring human OTC protein while retaining substantial OTC protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 5. In some embodiments, an mRNA suitable for the present invention encodes a protein substantially identical to human OTC protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 5. In some embodiments, an mRNA suitable for the present invention encodes a fragment or a portion of human OTC protein. In some embodiments, an mRNA suitable for the present invention encodes a fragment or a portion of human OTC protein, wherein the fragment or portion of the protein still maintains OTC activity similar to that of the wild-type protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 1, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 14 or SEQ ID NO: 15.

In some embodiments, a suitable mRNA encodes a fusion protein comprising a full length, fragment or portion of an OTC protein fused to another protein (e.g., an N or C terminal fusion). In some embodiments, the protein fused to the mRNA encoding a full length, fragment or portion of an OTC protein encodes a signal or a cellular targeting sequence.

Delivery Vehicles

According to the present invention, mRNA encoding an OTC protein (e.g., a full length, fragment or portion of an OTC protein) as described herein may be delivered as naked RNA (unpackaged) or via delivery vehicles. As used herein, the terms "delivery vehicle," "transfer vehicle," "nanoparticle" or grammatical equivalent, are used interchangeably.

In some embodiments, mRNAs encoding an OTC protein may be delivered via a single delivery vehicle. In some embodiments, mRNAs encoding an OTC protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired mRNA to a target cell or tissue.

Cationic Lipids

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z, 18Z)—N,N-dimethyl-6-(9Z, 12Z)-octadeca-9, 12-dien-1-yl) tetracosa-15,18-dien-1-amine (HGT5000), (15Z, 18Z)—N, N-dimethyl-6-((9Z, 12Z)-octadeca-9, 12-dien-1-yl)tetracosa-4,15,18-trien-1-amine (HGT5001), and (15Z,18Z)—N,N-dimethyl-6-((9Z, 12Z)-octadeca-9, 12-dien-1-yl) tetracosa-5, 15, 18-trien-1-amine (HGT5002).

In some embodiments, provided liposomes include a cationic lipid described in WO 2013/063468, filed Oct. 26, 2012 and in U.S. provisional application 61/953,516, filed Mar. 14, 2014, both of which are incorporated by reference herein.

In some embodiments, a cationic lipid comprises a compound of formula I-c1-a:

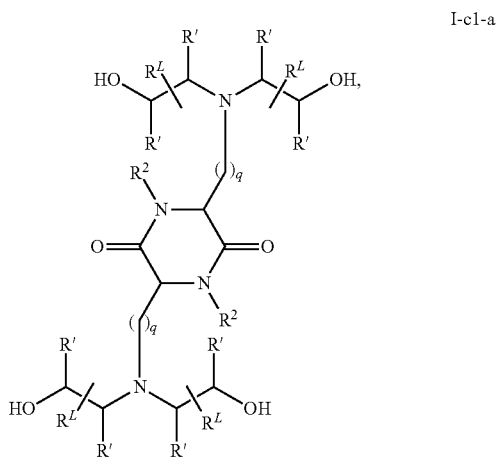

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

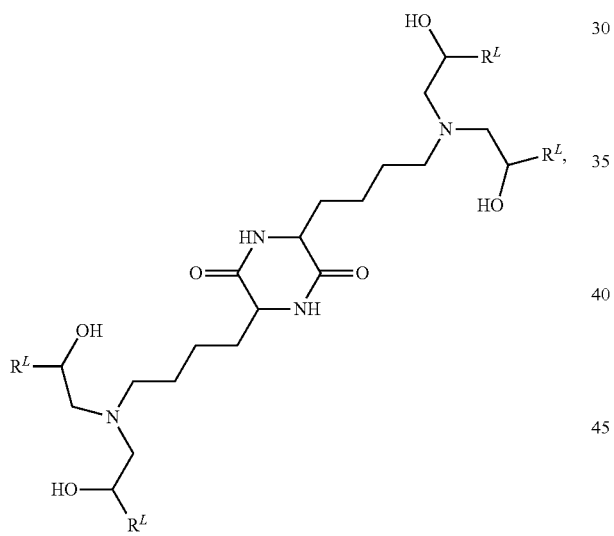

I-g or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione). Structure of cKK-E12 is shown below:

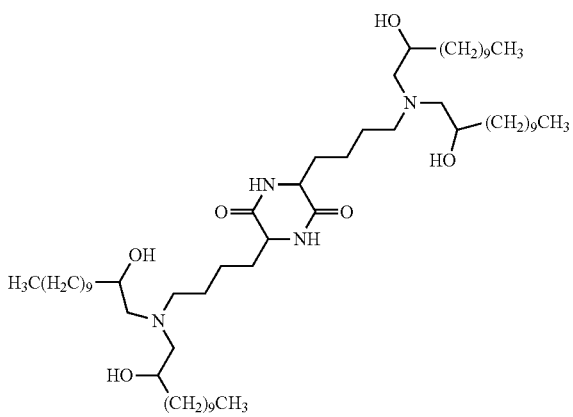

Additional exemplary cationic lipids include those of formula I:

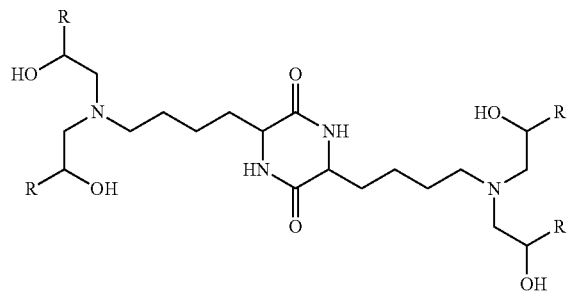

I and pharmaceutically acceptable salts thereof, wherein,

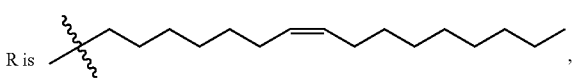 ("OF-00")

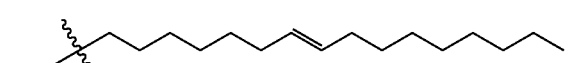 ("OF-01")

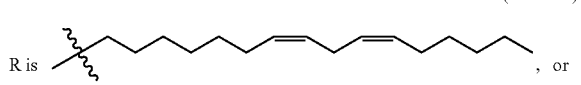 ("OF-02")

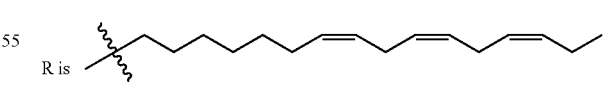 ("OF-03")

(see, e.g., Fenton, Owen S., et al. "Bioinspired Alkenyl Amino Alcohol Ionizable Lipid Materials for Highly Potent In Vivo mRNA Delivery." *Advanced materials* (2016)).

In some embodiments, the one or more cationic lipids may be N-[1-(2,3-dioleyloxy)propyl]-N,N,N-trimethylammonium chloride or "DOTMA" (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido) ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-di stearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethylaminoethyl-[1,3]-dioxolane or "DLin-K-XTC2-DMA", and 2-(2,2-di((9Z, 12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6a5)-N,N-dimethyl-2,2-di((9Z, 12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617, 468, the teachings of which are incorporated herein by reference in their entirety) or HGT5001 (cis or trans) (Provisional Patent Application No. 61/617,468), aminoalcohol lipoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., cKK-E12) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivitized lipids of the present invention may comprise a molar ratio from about 0% to about 15%, about 0.5% to about 15%, about 1% to about 15%, about 4% to about 10%, or about 2% of the total lipid present in the liposome.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkylcyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEGylated lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEGylated lipid(s) may be between about 30-60:25-35:20-30:1-15, respectively. In some embodiments, the ratio of cationic lipid(s) to non-cationic lipid(s) to cholesterol-based lipid(s) to PEGylated lipid(s) is approximately 40:30:20:10, respectively. In some embodiments, the ratio of cationic lipid(s) to non-cationic lipid(s) to cholesterol-based lipid(s) to PEGylated lipid(s) is approximately 40:30:25:5, respectively. In some embodiments, the ratio of cationic lipid(s) to non-cationic lipid(s) to cholesterol-based lipid(s) to PEGylated lipid(s) is approximately 40:32:25:3, respectively. In some embodiments, the ratio of cationic lipid(s) to non-cationic lipid(s) to cholesterol-based lipid(s) to PEGylated lipid(s) is approximately 50:25:20:5.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., OTC-encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., OTC-encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs (e.g., OTC-encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., OTC-encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs (e.g., OTC-encoding mRNAs) include a 3' poly(A) tail structure. A poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —$OCH_3$.

Additional cap analogs include, but are not limited to, a chemical structures selected from the group consisting of m⁷GpppG, m⁷GpppA, m⁷GpppC; unmethylated cap analogs (e.g., GpppG); dimethylated cap analog (e.g., m$^{2'7}$GpppG), trimethylated cap analog (e.g., m$^{2,2,7}$GpppG), dimethylated symmetrical cap analogs (e.g., m⁷Gpppm⁷G), or anti reverse cap analogs (e.g., ARCA; m$^{7,2'Ome}$GpppG, m$^{72'd}$GpppG, m$^{7,3'Ome}$GpppG, m$^{7,3'd}$GpppG and their tetraphosphate derivatives) (see, e.g., Jemielity, J. et al., "Novel 'antireverse' cap analogs with superior translational properties", RNA, 9: 1108-1122 (2003)).

In some embodiments, a suitable cap is a 7-methyl guanylate ("m⁷G") linked via a triphosphate bridge to the 5'-end of the first transcribed nucleotide, resulting in m⁷G(5')ppp(5')N, where N is any nucleoside. A preferred embodiment of a m⁷G cap utilized in embodiments of the invention is m⁷G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m⁷G cap analogs are known in the art, many of which are commercially available. These include the m⁷GpppG described above, as well as the ARCA 3'-OCH₃ and 2'-OCH₃ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Formation of Liposomes

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more liposomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Alternatively or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Provided methods of the present invention contemplate single as well as multiple administrations of a therapeutically effective amount of the therapeutic agents (e.g., mRNA encoding a OTC protein) described herein. Therapeutic agents can be administered at regular intervals, depending on the nature, severity and extent of the subject's condition (e.g., OTC deficiency). In some embodiments, a therapeutically effective amount of the therapeutic agents (e.g., mRNA encoding a OTC protein) of the present invention may be administered intrathecally periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily or every other day. In a preferred embodiment, the compositions of the present invention are administered to a subject twice a week, once a week, once every 7 days, once every 10 days, once every 14 days, once every 28 days, once every 30 days, once every two weeks, once every three weeks, or more preferably once every four weeks, once a month, twice a month, once every six weeks, once every eight weeks, once every other month, once every three months, once every four months, once every six months, once every eight months, once every nine months or annually. Also contemplated are compositions and liposomes which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating OTC deficiency). For example, a therapeutically effective amount may be an amount sufficient to achieve a desired therapeutic and/or prophylactic effect. Generally, the amount of a therapeutic agent (e.g., mRNA encoding a OTC protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg. In some embodiments, the therapeutically effective dose of 1.0 mg/kg is administered intramuscularly or intravenously.

Also contemplated herein are lyophilized pharmaceutical compositions comprising one or more of the liposomes disclosed herein and related methods for the use of such compositions as disclosed for example, in International Patent Application PCT/US12/41663, filed Jun. 8, 2012, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the OTC mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

In some embodiments, administering the provided composition results in an increased OTC mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased OTC mRNA expression level by at least about 10%, 20%, 30%, 40%, 50%, 60%, 70%, 80%, 90%, or 95% as compared to the baseline level immediately before treatment. In some embodiments, administering the provided composition results in an increased OTC mRNA expression level as compared to a OTC mRNA expression level in subjects who are not treated According to the present invention, a therapeutically effective dose of the provided composition, when administered regularly, results in an increased OTC protein expression or activity level in a subject as compared to a baseline OTC protein expression or activity level before treatment. Typically, the OTC protein expression or activity level is measured in a biological sample obtained from the subject such as blood, plasma or serum, urine, or solid tissue extracts. The baseline level is measured immediately before treatment. In some embodiments, administering the provided composition results in an increased OTC protein expression or activity level in a biological sample (e.g., plasma/serum or urine) by at least about 10%, 20%, 30%, 40%, 50%, 60%, 70%, 80%, 90%, or 95% as compared to a baseline level before treatment. In some embodiments, administering the provided composition results in an increased OTC protein expression or activity level in a biological sample (e.g., plasma/serum or urine) by at least about 10%, 20%, 30%, 40%, 50%, 60%, 70%, 80%, 90%, or 95% as compared to a baseline level before treatment for at least 24 hours, at least 48 hours, at least 72 hours, at least 3 days, at least 4 days, at least 5 days, at least 6 days, at least 7 days, at least 8 days, at least 9 days, at least 10 days, at least 11 days, at least 12 days, at least 13 days, at least 14 days, or at least 15 days.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, 96 hours, 1 week, 2 weeks, or 1 month after administration of provided liposomes and/or compositions.

In some embodiments, a therapeutically effective dose of the provided composition, when administered regularly, results in an increased citrulline production in a subject as compared to a baseline citrulline production before treatment. Typically, the citrulline level before or after the treatment may be measured in a biological sample obtained from the subject such as, blood, plasma or serum, urine, or solid tissue extracts. In some embodiments, treatment according to the present invention results in an increase of the citrulline level in a biological sample (e.g., plasma, serum, or urine) by at least 10%, 20%, 30%, 40%, 50%, 60%, 70%, 80%, 90%, 1-fold, 1.5-fold, 2-fold, 2.5-fold, or 3-fold as compared to the basedline citrulline level, respectively.

According to the present invention, a therapeutically effective dose of the provided composition, when administered regularly, results in at least one symptom or feature of the OTC deficiency is reduced in intensity, severity, or frequency or has delayed onset. In some embodiments, a therapeutically effective dose of the provided composition, when administered regularly, results in a reduced orotic acid level in a subject as compared to a baseline orotic acid level before treatment. In some embodiments, a therapeutically effective dose of the provided composition, when administered regularly, results in a reduced ammonia level in a subject as compared to a baseline ammonia level before treatment. In some embodiments, a therapeutically effective dose of the provided composition, when administered regularly, results in a reduced glutamine level in a subject as compared to a baseline glutamine level before treatment.

Typically, the orotic acid, ammonia or glutamine level before or after the treatment may be measured in a biological sample obtained from the subject such as, blood, plasma, serum, urine, or solid tissue extracts. The baseline orotic acid, ammonia or glutamine level is measured immediately before treatment. In some embodiments, treatment according to the present invention results in an reduction of the orotic acid, ammonia, or glutamine level in a biological sample (e.g., blood, serum, or urine) obtained from the subject by at least 10%, 20%, 30%, 40%, 50%, 60%, 70%, 80%, 90%, or 95% as compared to the baseline orotic acid, ammonia, or glutamine level, respectively. In some embodiments, a therapeutically effective dose of the provided composition, when administered regularly, results in a reduced plasma ammonia level to less than about 500

μmol/L, 400 μmol/L, 300 μmol/L, 200 μmol/L, 150 μmol/L, or 100 μmol/L. In some embodiments, a therapeutically effective dose of the provided composition, when administered regularly, results in a reduced plasma glutamine level to less than about 800 μmol/L, 700 μmol/L, or 600 μmol/L. In some embodiments, a therapeutically effective dose of the provided composition, when administered regularly, results in a reduced urinary orotic acid level to less than about 20 μmol/mmol creatinine, 15 μmol/mmol creatinine, or 10 μmol/mmol creatinine.

In some embodiments, administering the provided composition results in an increased OTC protein level in the liver of a subject as compared to a baseline level before treatment. Typically, the baseline level is measured immediately before treatment. In some embodiments, administering the provided composition results in an increased OTC protein level in the liver by at least about 10%, 20%, 30%, 40%, 50%, 60%, 70%, 80%, 90%, or 95% as compared to a baseline level before treatment. In some embodiments, administering the provided composition results in an increased OTC protein level in the liver as compared to a OTC protein level in the liver of subjects who are not treated.

In some embodiments, administering the provided composition results in an increased level of OTC protein in a liver cell (e.g., a hepatocyte) of a subject as compared to a baseline level before treatment. Typically, the baseline level is measured immediately before treatment. In some embodiments, administering the provided composition results in an increased OTC protein level in the liver cell by at least about 10%, 20%, 30%, 40%, 50%, 60%, 70%, 80%, 90%, or 95% as compared to a baseline level before treatment. In some embodiments, administering the provided composition results in an increased OTC protein level in a liver cell as compared to the OTC protein level a liver cell of subjects who are not treated.

In some embodiments, administering the provided composition results in an increased OTC protein level in plasma or serum of subject as compared to a baseline level before treatment. Typically, the baseline level is measured immediately before treatment. In some embodiments, administering the provided composition results in an increased OTC protein level in plasma or serum by at least about 10%, 20%, 30%, 40%, 50%, 60%, 70%, 80%, 90%, or 95% as compared to a baseline level before treatment. In some embodiments, administering the provided composition results in an increased OTC protein level in plasma or serum as compared to an OTC protein level in plasma or serum of subjects who are not treated.

In some embodiments, administering the provided composition results in increased OTC enzyme activity in a biological sample from a subject as compared to the baseline level before treatment. Typically, the baseline level is measured immediately before treatment. Biological samples include, for example, whole blood, serum, plasma, urine and tissue samples (e.g., liver). In some embodiments, administering the provided composition results in an increased OTC enzyme activity by at least about 10%, 20%, 30%, 40%, 50%, 60%, 70%, 80%, 90%, or 95% as compared to a baseline level immediately before treatment. In some embodiments, administering the provided composition results in an increased OTC enzyme activity as compared to OTC enzyme activity in subjects who are not treated.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, and/or 96 hours after administration of provided liposomes and/or compositions. In some embodiments, the expression of the protein encoded by delivered mRNA is detectable 1 week, two weeks, and/or 1 month after administration.

EXAMPLES

While certain compounds, compositions and methods of the present invention have been described with specificity in accordance with certain embodiments, the following examples serve only to illustrate the compounds of the invention and are not intended to limit the same.

Example 1. Exemplary Liposome Formulations for OTC mRNA Delivery and Expression

This example provides exemplary liposome formulations for effective delivery and expression of OTC mRNA in vivo.

Lipid Materials

The formulations described herein include a multi-component lipid mixture of varying ratios employing one or more cationic lipids, helper lipids (e.g., non-cationic lipids and/or cholesterol-based lipids) and PEGylated lipids designed to encapsulate mRNA encoding OTC protein. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" *J. Contr. Rel.* 2005, 107, 276-287), DLin-KC2-DMA (Semple, S. C. et al. "Rational Design of Cationic Lipids for siRNA Delivery" *Nature Biotech.* 2010, 28, 172-176), C12-200 (Love, K. T. et al. "Lipid-like materials for low-dose in vivo gene silencing" *PNAS* 2010, 107, 1864-1869), cKK-E12 (3,6-bis(4-(bis(2-hydroxydodecyl)amino)butyl)piperazine-2,5-dione), HGT5000, HGT5001, HGT4003, ICE, OF-02, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of $C_6$-$C_{20}$ length.

Codon-optimized human ornithine transcarbamylase (OTC) messenger RNA was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" *J. Gen. Virology* 2005, 86, 1239-1249) and a 3' poly(A) tail of approximately 250 nucleotides in length as determined by gel electrophoresis. 5' and 3' untranslated regions present in each mRNA product are represented as X and Y, respectively and defined as stated (vide infra).

Exemplary Codon-Optimized Human Ornithine Transcarbamylase (OTC) mRNAs
Construct Design:
  X-SEQ ID NO: 3-Y
  X-SEQ ID NO: 7-Y
5' and 3' UTR Sequences
  X (5' UTR Sequence)=

(SEQ ID NO: 11)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

Y (3' UTR Sequence)=

(SEQ ID NO: 12)
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

AAGCU

OR (SEQ ID NO: 13)
GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AGCU

An exemplary codon-optimized human OTC mRNA sequence includes SEQ ID NO: 3 or SEQ ID NO: 7 as described in the detailed description section.

An exemplary full-length codon-optimized human ornithine transcarbamylase (OTC) messenger RNA sequence is shown below:

(SEQ ID NO: 14)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGCUGUUCA

ACCUUCGGAUCUUGCUGAACAACGCUGCGUUCCGGAAUGGUCACAACUUC

AUGGUCCGGAACUUCAGAUGCGGCCAGCCGCUCCAGAACAAGGUGCAGCU

CAAGGGGAGGGACCUCCUCACCCUGAAAAACUUCACCGGAGAAGAGAUCA

AGUACAUGCUGUGGCUGUCAGCCGACCUCAAAUUCCGGAUCAAGCAGAAG

GGCGAAUACCUUCCUUUGCUGCAGGGAAAGUCCCUGGGGAUGAUCUUCGA

GAAGCGCAGCACUCGCACUAGACUGUCAACUGAAACCGGCUUCGCGCUGC

UGGGAGGACACCCCUGCUUCCUGACCACCCAAGAUAUCCAUCUGGGUGUG

AACGAAUCCCUCACCGACACAGCGCGGGUGCUGUCGUCCAUGGCAGACGC

GGUCCUCGCCCGCGUGUACAAGCAGUCUGAUCUGGACACUCUGGCCAAGG

AAGCCUCCAUUCCUAUCAUUAAUGGAUUGUCCGACCUCUACCAUCCCAUC

CAGAUUCUGGCCGAUUAUCUGACUCUGCAAGAACAUUACAGCUCCCUGAA

GGGGCUUACCCUUUCGUGGAUCGGCGACGGCAACAACAUUCUGCACAGCA

UUAUGAUGAGCGCUGCCAAGUUUGGAAUGCACCUCCAAGCAGCGACCCCG

AAGGGAUACGAGCCAGACGCCUCCGUGACGAAGCUGGCUGAGCAGUACGC

CAAGGAGAACGGCACUAAGCUGCUGCUCACCAACGACCCUCUCGAAGCCG

CCCACGGUGGCAACGUGCUGAUCACCGAUACCUGGAUCUCCAUGGGACAG

GAGGAGGAAAAGAAGAAGCGCCUGCAAGCAUUUCAGGGGUACCAGGUGAC

UAUGAAAACCGCCAAGGUCGCCGCCUCGGACUGGACCUUCUUGCACUGUC

UGCCCAGAAAGCCCGAAGAGGUGGACGACGAGGUGUUCUACAGCCCGCGG

UCGCUGGUCUUUCCGGAGGCCGAAAACAGGAAGUGGACUAUCAUGGCCGU

GAUGGUGUCCCUGCUGACCGAUUACUCCCCGCAGCUGCAGAAACCAAAGU

UCUGACGGGUGGCAUCCCUGUGACCCCUCCCCAGUGCCUCUCCUGGCCCU

GGAAGUUGCCACUCCAGUGCCCACCAGCCUUGUCCUAAUAAAAUUAAGUU

GCAUCAAGCU.

In another example, a full length codon-optimized human ornithine transcarbamylase (OTC) messenger RNA sequence is shown below:

(SEQ ID NO: 15)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGCUGUUCA

ACCUUCGGAUCUUGCUGAACAACGCUGCGUUCCGGAAUGGUCACAACUUC

AUGGUCCGGAACUUCAGAUGCGGCCAGCCGCUCCAGAACAAGGUGCAGCU

CAAGGGGAGGGACCUCCUCACCCUGAAAAACUUCACCGGAGAAGAGAUCA

AGUACAUGCUGUGGCUGUCAGCCGACCUCAAAUUCCGGAUCAAGCAGAAG

GGCGAAUACCUUCCUUUGCUGCAGGGAAAGUCCCUGGGGAUGAUCUUCGA

GAAGCGCAGCACUCGCACUAGACUGUCAACUGAAACCGGCUUCGCGCUGC

UGGGAGGACACCCCUGCUUCCUGACCACCCAAGAUAUCCAUCUGGGUGUG

AACGAAUCCCUCACCGACACAGCGCGGGUGCUGUCGUCCAUGGCAGACGC

GGUCCUCGCCCGCGUGUACAAGCAGUCUGAUCUGGACACUCUGGCCAAGG

AAGCCUCCAUUCCUAUCAUUAAUGGAUUGUCCGACCUCUACCAUCCCAUC

CAGAUUCUGGCCGAUUAUCUGACUCUGCAAGAACAUUACAGCUCCCUGAA

GGGGCUUACCCUUUCGUGGAUCGGCGACGGCAACAACAUUCUGCACAGCA

UUAUGAUGAGCGCUGCCAAGUUUGGAAUGCACCUCCAAGCAGCGACCCCG

AAGGGAUACGAGCCAGACGCCUCCGUGACGAAGCUGGCUGAGCAGUACGC

CAAGGAGAACGGCACUAAGCUGCUGCUCACCAACGACCCUCUCGAAGCCG

CCCACGGUGGCAACGUGCUGAUCACCGAUACCUGGAUCUCCAUGGGACAG

GAGGAGGAAAAGAAGAAGCGCCUGCAAGCAUUUCAGGGGUACCAGGUGAC

UAUGAAAACCGCCAAGGUCGCCGCCUCGGACUGGACCUUCUUGCACUGUC

UGCCCAGAAAGCCCGAAGAGGUGGACGACGAGGUGUUCUACAGCCCGCGG

UCGCUGGUCUUUCCGGAGGCCGAAAACAGGAAGUGGACUAUCAUGGCCGU

-continued

GAUGGUGUCCCUGCUGACCGAUUACUCCCCGCAGCUGCAGAAACCAAAGU

UCUGAGGGUGGCAUCCCUGUGACCCCUCCCCAGUGCCUCUCCUGGCCCUG

GAAGUUGCCACUCCAGUGCCCACCAGCCUUGUCCUAAUAAAAUUAAGUUG

CAUCAAAGCU.

In another example, a full length codon-optimized human ornithine transcarbamylase (OTC) messenger RNA sequence is shown below:

(SEQ ID NO: 4)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGCUGUUUA

ACCUGAGAAUUCUGCUGAACAACGCCGCGUUCAGGAACGGCCACAAUUUC

AUGGUCCGCAACUUUAGAUGCGGACAGCCUCUCCAAAACAAGGUCCAGCU

CAAGGGGCGGGACUUGCUGACCCUUAAGAACUUUACCGGCGAAGAGAUCA

AGUACAUGCUGUGGUUGUCAGCGGACCUGAAGUUCCGCAUCAAGCAGAAA

GGGGAGUAUCUGCCGCUGCUCCAAGGAAAGUCGCUCGGCAUGAUCUUCGA

GAAGCGCUCGACCAGAACCCGGCGUGCCACUGAAACUGGGUUUCGCCCUUC

UGGGUGGACACCCUUGUUUCCUGACAACCCAGGACAUCCAUCUGGGCGUG

AACGAAAGCCUCACUGACACCGCCAGGGUGCUGAGCUCCAUGGCCGACGC

UGUCCUUGCCCGGGUGUACAAGCAGUCCGAUCUGGACACUCUGGCCAAGG

AAGCGUCCAUCCCGAUCAUUAACGGACUGUCCGACCUGUACCACCCGAUC

CAGAUUCUGGCCGACUACCUGACCUUGCAAGAGCACUACAGCUCACUGAA

GGGCUUGACCCUGAGCUGGAUCGGCGACGGAAACAACAUUCUGCAUUCGA

UCAUGAUGUCCGCGGCCAAGUUCGGAAUGCAUCUGCAGGCCGCAACUCCC

AAGGGAUACGAACCUGAUGCGUCCGUGACUAAGCUGGCCGAGCAGUACGC

AAAGGAAAACGGCACCAAGCUGCUGCUGACCAACGACCCGCUCGAAGCUG

CCCACGGAGGGAACGUGCUCAUUACCGACACUUGGAUCUCCAUGGGGCAG

GAAGAAGAGAAGAAGAAGCGGCUCCAGGCAUUCCAGGGUUACCAGGUCAC

CAUGAAAACGGCCAAAGUGGCCGCUUCGGAUUGGACUUUCCUCCACUGCC

UUCCCCGCAAACCUGAGGAAGUGGAUGAUGAAGUGUUCUACUCCCCACGC

UCCCUCGUGUUCCCCGAGGCCGAGAAUCGGAAGUGGACCAUUAUGGCCGU

GAUGGUGUCACUGCUGACCGACUACAGCCCCCAACUGCAAAAGCCGAAGU

UCUGACGGGUGGCAUCCCUGUGACCCCUCCCCAGUGCCUCUCCUGGCCCU

GGAAGUUGCCACUCCAGUGCCCACCAGCCUUGUCCUAAUAAAAUUAAGUU

GCAUCAAGCU

Exemplary Formulation Protocols

A. cKK-E12

Aliquots of 50 mg/mL ethanolic solutions of cKK-E12, DOPE, cholesterol and DMG-PEG2K were mixed and diluted with ethanol to 3 mL final volume. Separately, an aqueous buffered solution (10 mM citrate/150 mM NaCl, pH 4.5) of OTC mRNA was prepared from a 1 mg/mL stock. The lipid solution was injected rapidly into the aqueous mRNA solution and shaken to yield a final suspension in 20% ethanol. The resulting nanoparticle suspension was filtered, infiltrated with 1×PBS (pH 7.4), concentrated and stored at 2-8° C. The final concentration, $Z_{ave}$, $D_{V(50)}$ and $D_{V(90)}$ of the OTC encapsulated mRNA were determined.

B. C12-200

Aliquots of 50 mg/mL ethanolic solutions of C12-200, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $D_{V(50)}$ and $D_{V(90)}$ of the OTC encapsulated mRNA are determined.

C. HGT4003

Aliquots of 50 mg/mL ethanolic solutions of HGT4003, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $D_{V(50)}$ and $D_{V(90)}$ of the OTC encapsulated mRNA are determined.

D. ICE

Aliquots of 50 mg/mL ethanolic solutions of ICE, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $D_{V(50)}$ and $D_{V(90)}$ of the OTC encapsulated mRNA are determined.

E. HGT5001

Aliquots of 50 mg/mL ethanolic solutions of HGT5001, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $D_{V(50)}$ and $D_{V(90)}$ of the OTC encapsulated mRNA are determined.

F. HGT5000

Aliquots of 50 mg/mL ethanolic solutions of HGT5000, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $D_{V(50)}$ and $D_{V(90)}$ of the OTC encapsulated mRNA are determined.

G. DLinKC2DMA

Aliquots of 50 mg/mL ethanolic solutions of DLinKC2DMA, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $D_{V(50)}$ and $D_{V(90)}$ of the OTC encapsulated mRNA are determined.

H. DODAP

Aliquots of 50 mg/mL ethanolic solutions of DODAP, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $D_{V(50)}$ and $D_{V(90)}$ of the OTC encapsulated mRNA are determined.

I. DODMA

Aliquots of 50 mg/mL ethanolic solutions of DODMA, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $D_{V(50)}$ and $D_{V(90)}$ of the OTC encapsulated mRNA are determined.

Example 2. Intravenous Administration of OTC mRNA-Loaded Liposome Nanoparticles

This example illustrates exemplary methods of administering OTC mRNA-loaded liposome nanoparticles and methods for analyzing OTC mRNA in various target tissues in vivo.

All studies were performed using spf$^{ash}$ mice. Mice were treated with human OTC mRNA-loaded cKK-E12-based lipid nanoparticles by a single bolus tail-vein injection of a 0.5 mg/kg dose. Mice were sacrificed and perfused with saline at 24 hours, 72 hours, 8 days, 11 days and 15 days.

Tissues, such as liver, of each mouse were harvested, apportioned into separate parts, and stored in either 10% neutral buffered formalin or snap-frozen and stored at −80° C. for analysis.

Western Blot Detection of OTC Protein in Mouse Liver Homogenate

Samples were homogenized using a HEPES lysis buffer and freeze/thawed twice to ensure total cell lysis. Debris was pelleted and homogenate was assessed for total protein quantification by BCA assay. 10 ng total protein with NuPage Reducing agent and Loading dye was incubated 5 minutes at 95° C., followed by separation of proteins on an 8-16% tris/glycine SDS-PAGE gel. Proteins were transferred onto a PVDF membrane, blocked with a 2% i-Block solution in PBST, and then incubated with a proprietary anti-OTC antibody (22A03). Gels were washed, incubated with HRP-conjugated secondary antibody, washed again and developed using ECL-Prime substrate on a Konika Minolta SRX-101a film processor.

ELISA Quantification of OTC Protein in Mouse Liver Homogenate

Samples were homogenized using a HEPES lysis buffer and freeze/thawed twice to ensure total cell lysis. Debris was pelleted and supernatant was collected for the assay. A proprietary anti-OTC antibody (25D11) was coated onto a Nunc MaxiSorb plate at 1 μg/mL for 1 hour in 50 mM sodium bicarbonate solution, pH 9.6. The plate was washed using DPBS and Tween-20 wash buffer, then blocked 1 hour with Surmodics casein blocking buffer. The plates were again washed, and then samples and standard were added in duplicate and incubated for an additional hour. The plate was washed and then HRP-conjugated detection Ab (21C02) was added to the plate at a 1:5500 dilution and incubated for 1 hour. After a final wash, the plate was developed using Surmodics TMB substrate, stopped with 1N HCl and read at 450 nm minus 650 nm on a spectrophotometer.

Citrulline Activity Assay Using Mouse Liver Homogenates

Mouse liver homogenate was prepared as previously described. Homogenates were diluted in 1×DPBS to the desired concentration then added into UltraPure water in a 96-well plate. Citrulline standard was added in predetermined amounts to serve as the calibrators. A reaction mix containing carbamoyl phosphate, ornithine and triethanolamine was added to each well and the reaction was allowed to proceed at 37° C. for 30 minutes. The reaction was stopped with a mix of phosphoric and sulfuric acid, and diacetylmonoxime was added to each well. The plate was incubated at 85° C. for 30 minutes, cooled briefly, and read at 490 nm on a spectrophotometer.

Orotic Acid Quantification in Mouse Urine

The quantification of orotic acid from animal urine samples was performed via Ultra Performance Liquid Chromatography (UPLC) using an ion exchange column. Briefly, urine samples were diluted two-fold using RNase-free water and a portion was loaded onto a ThermoScientific 100× column. The mobile phase comprising acetonitrile and 25 mM ammonium acetate afforded separation and quantification of orotic acid with detection based on absorbance at 280 nm.

Ammonia Quantification in Mouse Plasma

An aliquot of whole blood was collected into lithium heparin plasma tubes and processed to plasma. Fresh plasma samples were analyzed using an IDEXX Catalyst Dx analyzer.

Results

Detection of OTC protein in the livers of the treated mice was achieved using immunohistochemical methods (e.g. Western blot). As demonstrated in FIG. 1, the exogenous human OTC protein was detected at 24 hours, 72 hours, 8 days, 11 days and 15 days.

Figure 2A:
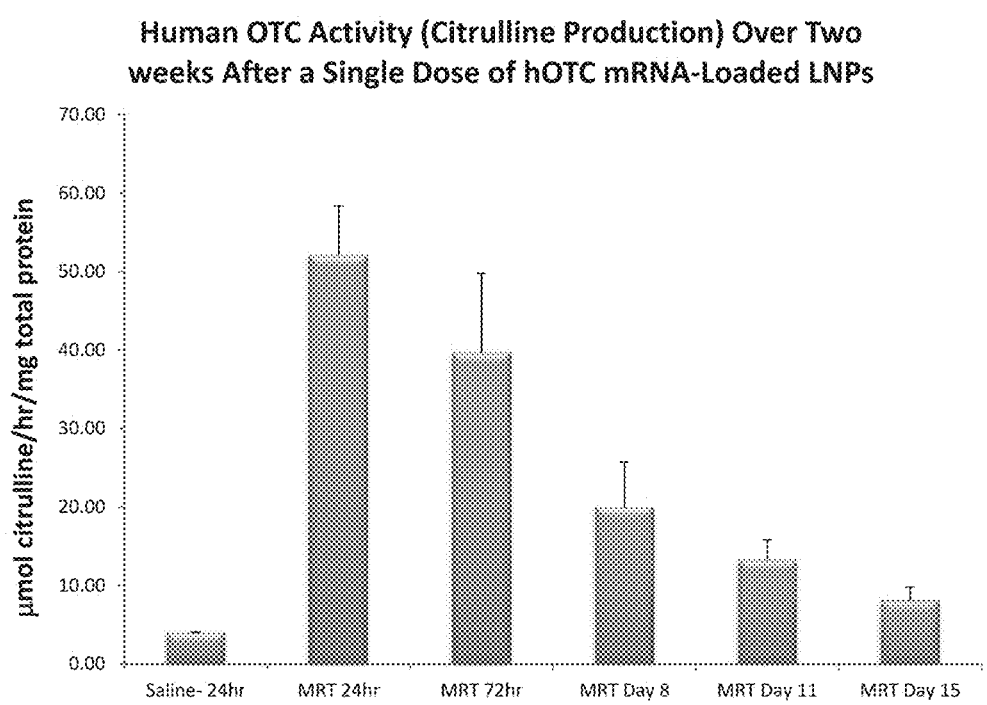
FIG. 2A depicts exemplary citrulline production in mice over a two-week period after a single 0.5 mg/kg dose of hOTC mRNA-loaded lipid nanoparticles.
Figure 2B:
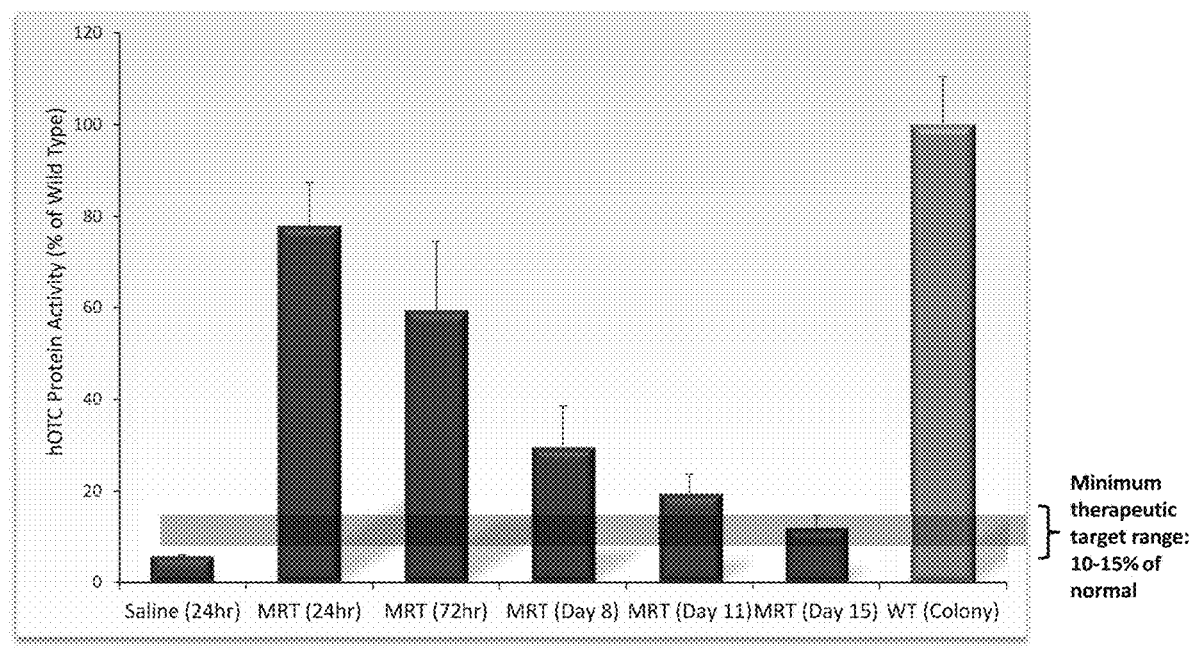
FIG. 2B depicts exemplary hOTC protein activity in mice, as a percentage of wild-type activity, over a two-week period after a single 0.5 mg/kg dose of hOTC mRNA-loaded lipid nanoparticles.
Figure 3A:
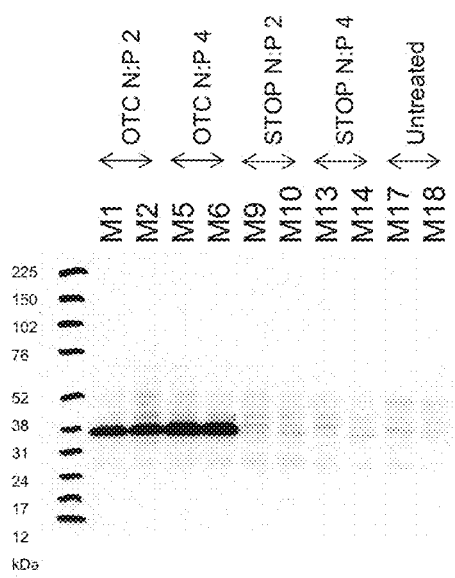
FIG. 3A depicts exemplary immunohistochemical detection of human OTC protein by Western blot after a single 0.5 mg/kg dose of hOTC mRNA-loaded lipid nanoparticles.
Figure 3B:
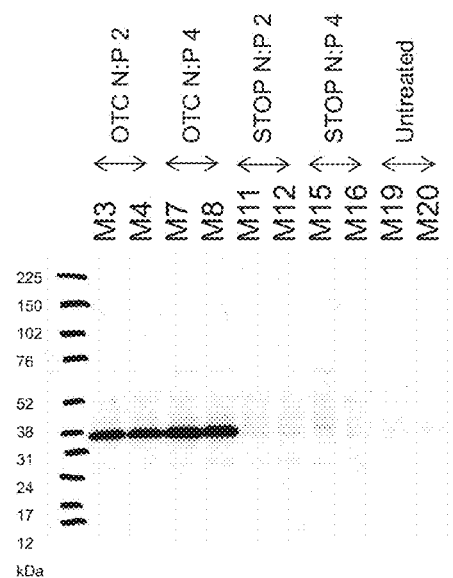
FIG. 3B depicts exemplary immunohistochemical detection of human OTC protein by Western blot after a single 0.5 mg/kg dose of hOTC mRNA-loaded lipid nanoparticles. The lipid nanoparticles used were different from those used in FIG. 3A.

Additionally, the mRNA-derived hOTC protein was also shown to be enzymatically active, as demonstrated by measuring levels of citrulline production using a custom ex vivo activity assay. The hOTC protein produced in mice by the hOTC mRNA-loaded lipid nanoparticles was active for over two weeks after a single 0.5 mg/kg dose of hOTC mRNA-loaded lipid nanoparticles (FIG. 2A). As illustrated in FIG. 2B, the single 0.5 mg/kg dose of hOTC mRNA-loaded lipid nanoparticles resulted in hOTC protein activity above the minimum therapeutic target range of 10-15% of normal activity. Furthermore, the activity demonstrated at two weeks post-administration lead to citrulline levels approximately 3-fold over background levels.

mRNA-derived hOTC protein was also produced in spf$^{ash}$ mice when multiple hOTC mRNA lipid nanoparticle formulations were used (FIG. 3A and FIG. 3B). Two separate formulations were made using methods as described above which encapsulated CO-hOTC mRNA with different amounts of lipids. N:P 4 utilized twice as much total lipid as N:P 2 formulations. Also, similar control formulations (STOP N:P 2 and STOP N:P 4) incorporating nonsense mutated hOTC mRNA, when administered to spf$^{ash}$, did not produce any detectable hOTC protein. Separately, saline was used as another control treatment in this experiment. The isolated livers were homogenized and hOTC protein production and activity were determined as described above. FIG. 3A and FIG. 3B depict immunoblot analysis of representative mouse livers from each group. Positive detection of human OTC protein was observed for both formulations containing hOTC mRNA. No hOTC protein was observed for either nonsense mRNA-based control group or the saline-treated (untreated) mice.

Figure 4:
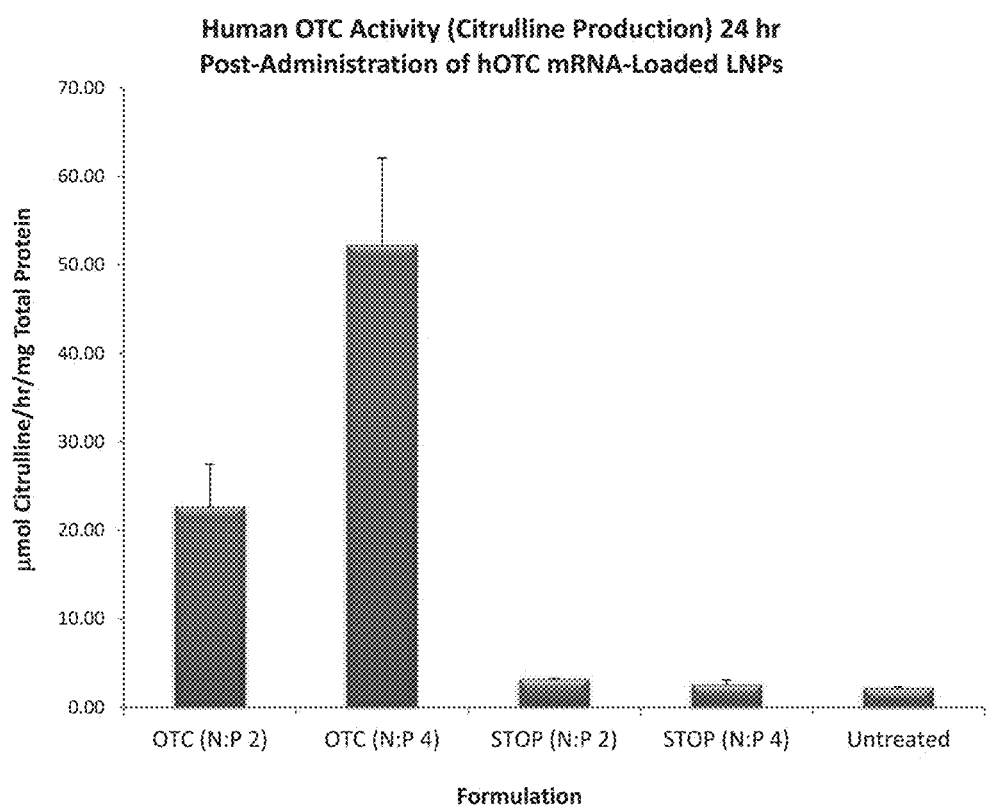
FIG. 4 depicts exemplary citrulline production in mice 24 hours after a single 0.5 mg/kg dose of hOTC mRNA-loaded lipid nanoparticles. No hOTC activity was observed in mice treated with nonsense mutated mRNA lipid nanoparticles (STOP).

FIG. 4 shows hOTC activity observed from each group. Substantial hOTC activity was observed in both groups treated with hOTC mRNA LNPs while no increase in activity was measured in the nonsense mutated mRNA control groups as compared to saline-treated (untreated) mice. This activity can be attributed to successful active, protein production derived from LNP-delivered hOTC mRNA. FIG. 4 demonstrates that the hOTC mRNA produced active hOTC protein capable of producing citrulline, while the control formulations, which did not produce detectable hOTC protein, did not show any citrulline-producing activity over background levels.

Figure 5:
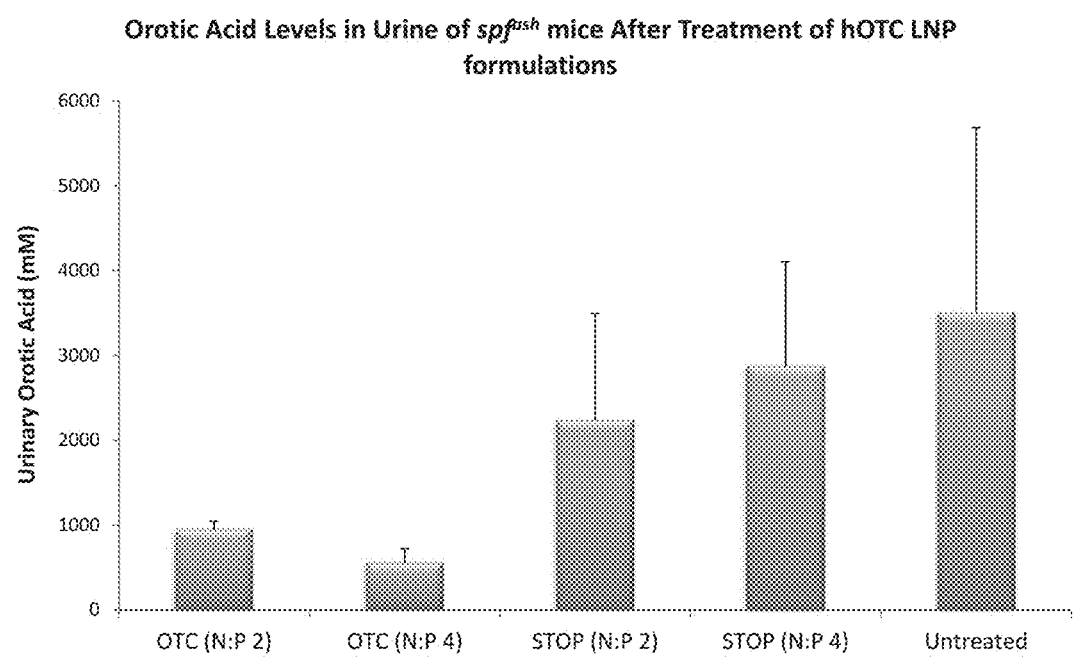
FIG. 5 depicts exemplary orotic acid levels in the urine of mice after a single 0.5 mg/kg dose of hOTC mRNA-loaded lipid nanoparticles.

Further, efficacy was demonstrated in this disease model through normalization of orotic acid levels in the urine of treated mice. Specifically, urine samples were obtained 24 hours post-administration of all formulations (and saline control, "untreated") and measured for orotic acid quantitation. Activity of the mRNA-derived hOTC protein in spf$^{ash}$ mice was determined by monitoring orotic acid, a known biomarker of OTC deficiency (FIG. 5). A clear decrease in orotic acid levels in urine was observed in mice treated with hOTC mRNA-loaded lipid nanoparticles, while no significant decrease in orotic acid was observed when mice were administered control formulations that comprised nonsense mutated hOTC mRNA.

Figure 6A:
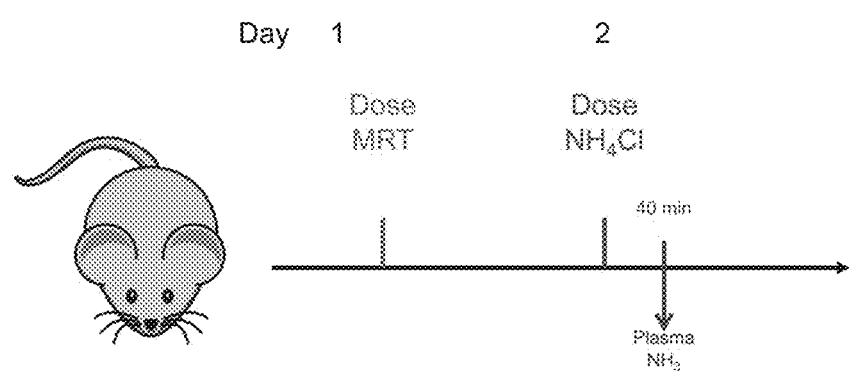
FIG. 6A depicts an exemplary dosing and testing scheme in Spf$^{ash}$ mice that involved an ammonia challenge.

In a separate study, spf$^{ash}$ mice were treated with two different hOTC mRNA LNP formulations (N/P=2, N/P=4) at two dose levels (0.50 mg/kg, 1.0 mg/kg). The test articles were administered as a single intravenous dose. As illustrated in FIG. 6A, after 24 hours (post-administration), the mice were presented with an ammonia challenge wherein a bolus injection of ammonium chloride (NH$_4$Cl) was administered intraperitoneally. This was performed to represent a hyperammonemic episode that a patient suffering from OTC deficiency could experience. Plasma ammonia levels were monitored 40 minutes after the NH$_4$Cl challenge.

Figure 6B:
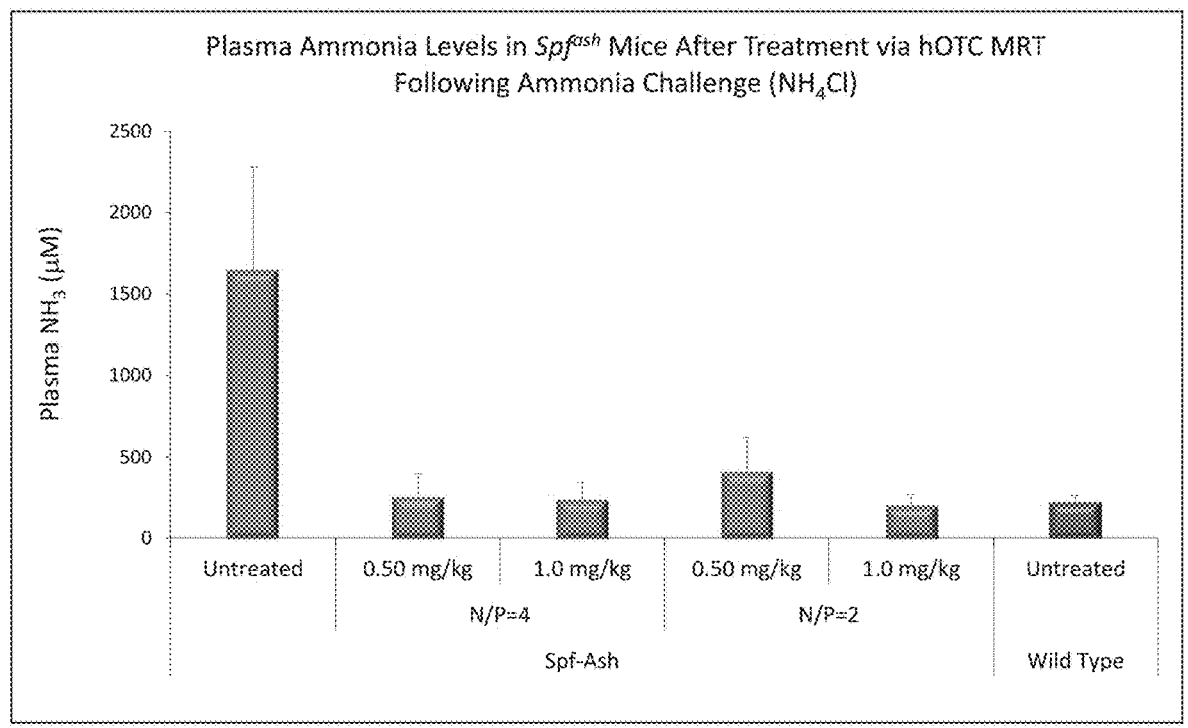
FIG. 6B depicts exemplary plasma ammonia levels in Spf$^{ash}$ mice after treatment with hOTC mRNA-loaded lipid nanoparticles following an ammonia challenge with NH$_4$Cl.
Figure 7:
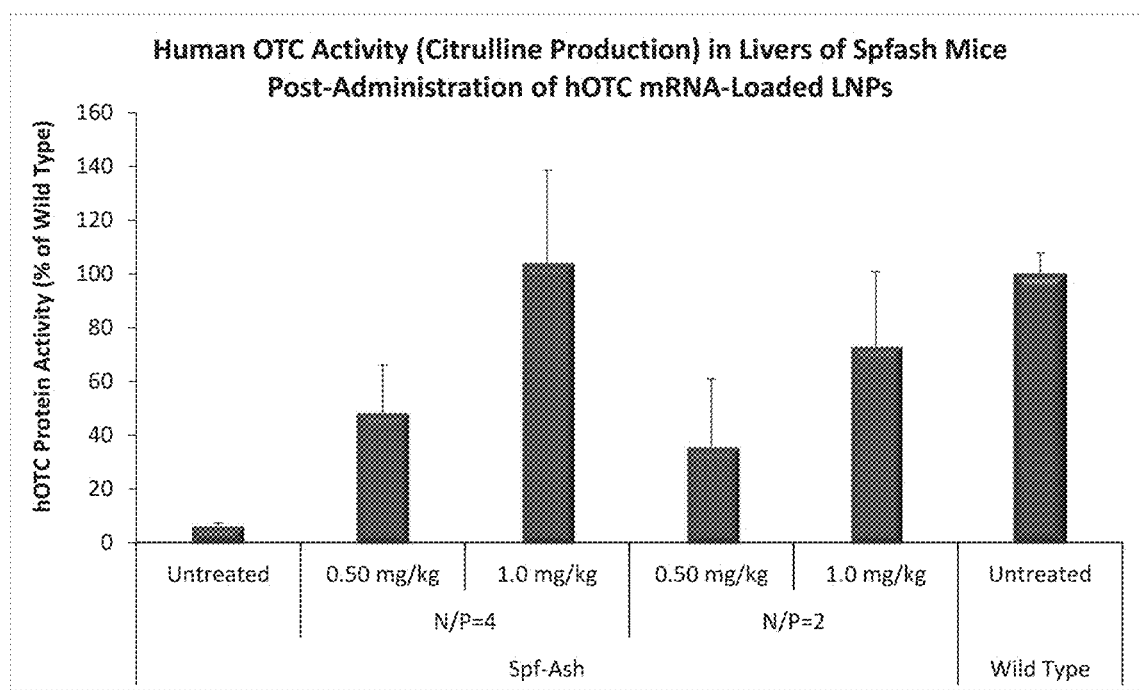
FIG. 7 depicts exemplary citrulline production in the livers of Spf$^{ash}$ mice after treatment with hOTC mRNA-loaded lipid nanoparticles, as a percentage of wild-type activity.

FIG. 6B compares plasma ammonia levels of the treated mice to those of both untreated spf$^{ash}$ mice as well as wild type mice. Complete protection of a hyperammonemic episode was achieved at all doses administered of the hOTC mRNA LNP formulations when normalized to wild type (untreated) ammonia levels. Untreated spf$^{ash}$ mice showed marked elevations in plasma ammonia under identical conditions. To confirm that this was due to the presence of active hOTC protein in the livers of these mice, livers were harvested and analyzed for OTC activity (FIG. 7). All doses administered produced activity levels from a range of 35%-103% normal activity as compared to wild type activity levels.

Example 3. Multi-Dose Administration of OTC mRNA-Loaded Liposome Nanoparticles

This example illustrates exemplary methods of administering OTC mRNA-loaded liposome nanoparticles over an extended time period and methods for analyzing OTC mRNA in various target tissues in vivo.

Figure 8:
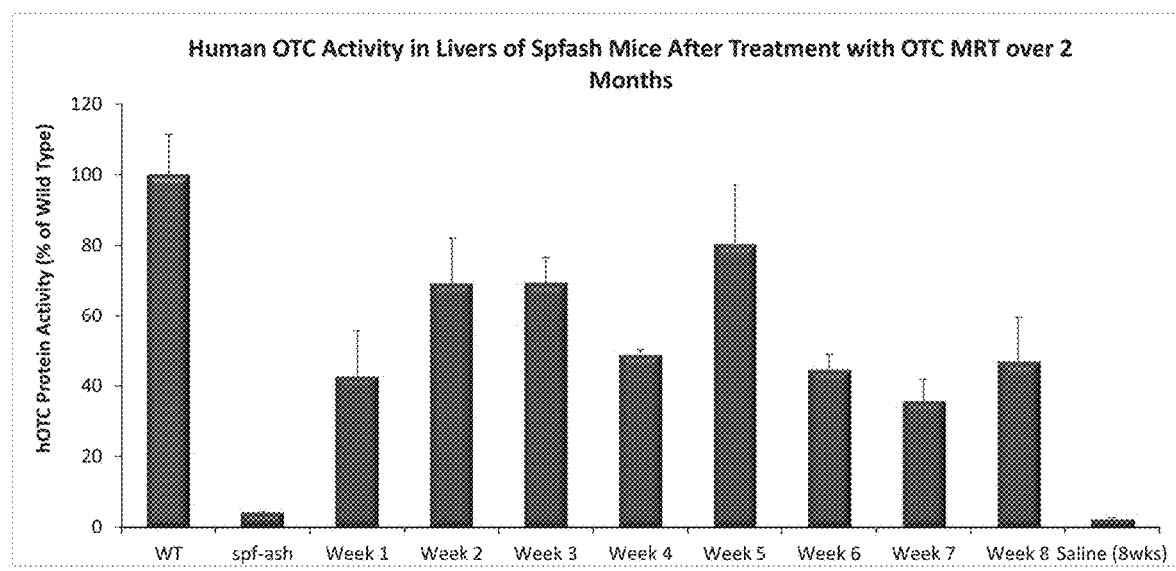
FIG. 8 depicts exemplary hOTC activity, as measured by citrulline production, in the livers of Spf$^{ash}$ mice after treatment with hOTC mRNA-loaded lipid nanoparticles over 8 weeks, as a percentage of wild-type activity.

The study was performed using spf$^{ash}$ mice. Mice were treated as described in Example 2, but in a multi-dose format. Specifically, a multi-dose study was conducted in spf$^{ash}$ mice which entailed 8 weekly doses of hOTC mRNA-loaded LNPs administered intravenously at 0.60 mg/kg. A cohort of mice was sacrificed each week and the livers were analyzed for hOTC activity and compared to wild-type OTC activity levels. The test article was well tolerated and liver enzymes remained within normal ranges for all doses. FIG. 8 shows human OTC activity produced in these treated mice as a percentage of wild-type levels. A level of at least approximately 36% of wild-type levels was maintained for all 8 weeks of dosing.

Figure 9A:
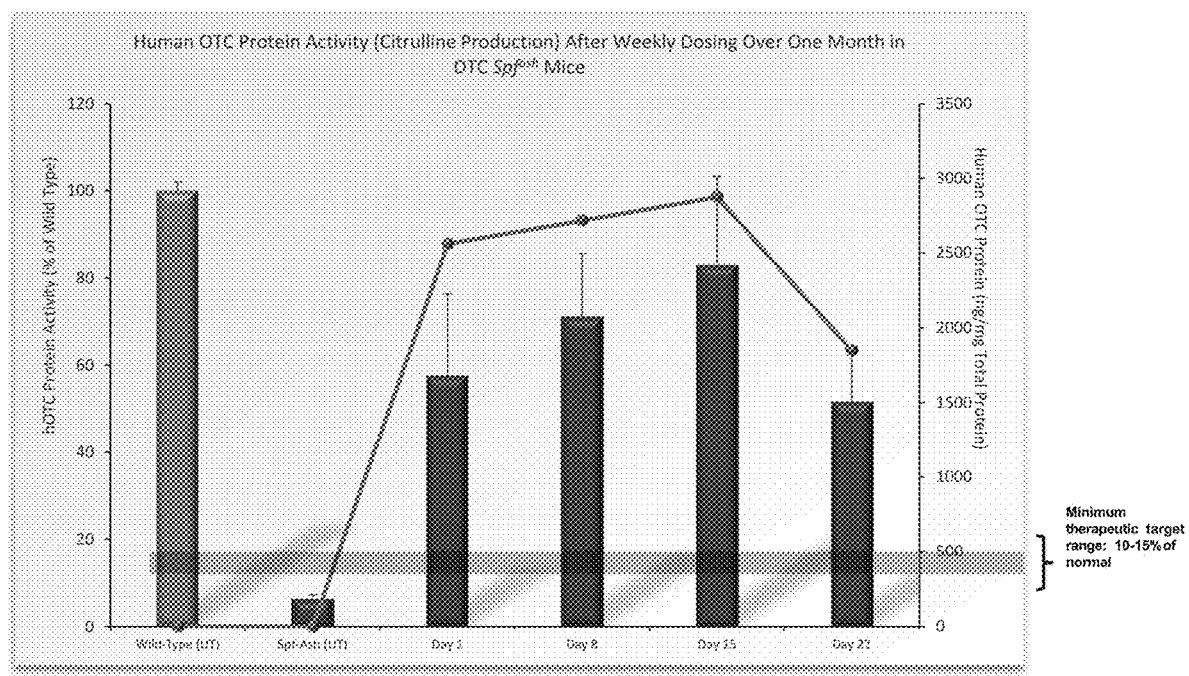
FIG. 9A depicts exemplary hOTC activity, as measured by citrulline production, in Spf$^{ash}$ mice after weekly treatment with hOTC mRNA-loaded lipid nanoparticles over one month.
Figure 9B:
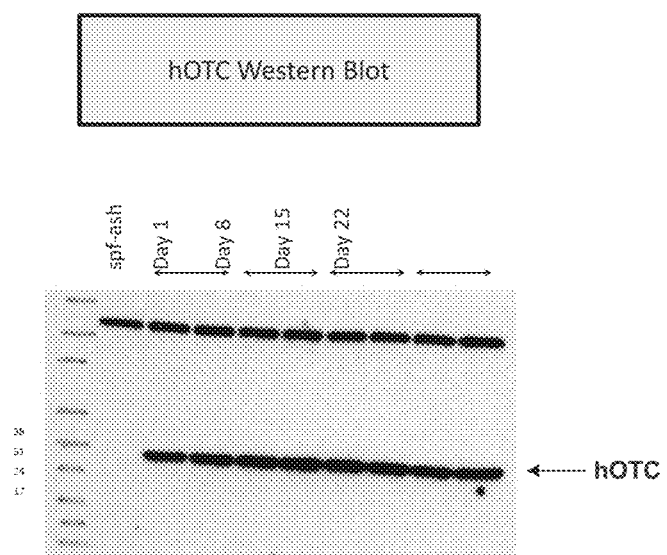
FIG. 9B depicts exemplary immunohistochemical detection of human OTC protein by Western blot after a weekly dosing (1.0 mg/kg) with hOTC mRNA-loaded lipid nanoparticles.

An additional multi-dose study was conducted as described in Example 2, but animals were administered 4 weekly doses of 1.0 mg/kg hOTC mRNA-loaded LNPs. FIG. 9A shows human OTC activity produced in these treated mice as a percentage of wild-type levels in spf$^{ash}$ mice that were dosed weekly with 1.0 mg/kg doses of hOTC mRNA-loaded LNPs. The multi-dose regimen produced therapeutic levels of active hOTC protein in the OTC-deficient mice for over three weeks. As demonstrated in FIG. 9B, the exogenous human OTC protein was detected at Day 1, Day 8, Day 15 and Day 22.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A pharmaceutical composition for treating ornithine transcarbamylase (OTC) deficiency, comprising an mRNA encoding an ornithine transcarbyamylase (OTC) protein and wherein the mRNA encoding the OTC protein comprises a polynucleotide sequence at least 80% identical to SEQ ID NO: 3, SEQ ID NO: 6, SEQ ID NO: 7, SEQ ID NO: 8, SEQ ID NO: 9 or SEQ ID NO: 10, wherein the mRNA encoding the OTC protein is codon optimized, and wherein the OTC protein encoded by the mRNA that is at least 80% identical to SEQ ID NO: 3, SEQ ID NO: 6, SEQ ID NO: 7, SEQ ID NO: 8, SEQ ID NO: 9 or SEQ ID NO: 10 comprises an amino acid sequence at least 98% identical to SEQ ID NO: 5.

2. A pharmaceutical composition for treating ornithine transcarbamylase (OTC) deficiency, comprising an mRNA encoding an ornithine transcarbyamylase (OTC) protein, wherein the mRNA comprises a polynucleotide sequence at least 85% identical to SEQ ID NO: 7, wherein the mRNA encoding the OTC protein is codon optimized, and wherein the OTC protein encoded by the mRNA that is at least 85% identical to SEQ ID NO: 7 comprises an amino acid sequence at least 98% identical to SEQ ID NO: 5.

3. The composition of claim 1, wherein the mRNA further comprises a 5' untranslated region (UTR) sequence of SEQ ID NO: 11.

4. The composition of claim 1, wherein the mRNA further comprises a 3' untranslated region (UTR) sequence of SEQ ID NO: 12 or SEQ ID NO: 13.

5. The composition of claim 1, wherein the mRNA is encapsulated within a liposome.

6. The composition of claim 5, wherein the liposome comprises one or more cationic lipids, one or more non-cationic lipids, one or more cholesterol-based lipids and one or more PEG-modified lipids.

7. The composition of claim 6, wherein the one or more cationic lipids comprise a cationic lipid selected from the group consisting of C12-200, MC3, DLinDMA, DLinkC2DMA, cKK-E12, ICE (Imidazole-based), HGT5000, HGT5001, OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

8. The composition of claim 6, wherein the one or more non-cationic lipids are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)) and combinations thereof.

9. The composition of claim 6, wherein the one or more cholesterol-based lipids are cholesterol and/or PEGylated cholesterol.

10. The composition of claim 5, wherein the liposome has a size less than about 100 nm.

11. The composition of claim 1, wherein the mRNA comprises one or more modified nucleotides.

12. The composition of claim 1, wherein the mRNA is unmodified.

13. The composition of claim 2, wherein the mRNA further comprises a 5' untranslated region (UTR) sequence of SEQ ID NO: 11.

14. The composition of claim 2, wherein the mRNA further comprises a 3' untranslated region (UTR) sequence of SEQ ID NO: 12 or SEQ ID NO: 13.

15. The composition of claim 14, wherein the mRNA is encapsulated within a liposome.

16. The composition of claim 15, wherein the liposome comprises one or more cationic lipids, one or more non-cationic lipids, one or more cholesterol-based lipids and one or more PEG-modified lipids.

17. The composition of claim 16, wherein the one or more cationic lipids comprise a cationic lipid selected from the group consisting of C12-200, MC3, DLinDMA, DLinkC2DMA, cKK-E12, ICE (Imidazole-based), HGT5000, HGT5001, OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

18. The composition of claim 16, wherein the one or more non-cationic lipids are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)) and combinations thereof.

19. The composition of claim 16, wherein the one or more cholesterol-based lipids are cholesterol and/or PEGylated cholesterol.

20. The composition of claim 15, wherein the liposome has a size less than about 100 nm.

21. The composition of claim 2, wherein the mRNA comprises one or more modified nucleotides.

22. The composition of claim 2, wherein the mRNA is unmodified.

23. The composition of claim 2, wherein the mRNA comprises a polynucleotide sequence at least 90% identical to SEQ ID NO:7.

24. The composition of claim 2, wherein the mRNA comprises a polynucleotide sequence at least 95% identical to SEQ ID NO:7.

* * * * *